United States Patent [19]
Boden et al.
[11] 4,420,423
[45] * Dec. 13, 1983

[54] METHYL SUBSTITUTED-2-OXOHEXANE DERIVATIVES AND PROCESS FOR PREPARING AND USING SAME

[75] Inventors: Richard M. Boden, Monmouth Beach; Lambert Dekker, Wyckoff; Frederick L. Schmitt, Holmdel, all of N.J.; Augustinus G. Van Loveren, Rye, N.Y.

[73] Assignee: International Flavors & Fragrances Inc., New York, N.Y.

[ * ] Notice: The portion of the term of this patent subsequent to Dec. 8, 1998 has been disclaimed.

[21] Appl. No.: 345,666

[22] Filed: Feb. 4, 1982

Related U.S. Application Data

[63] Continuation-in-part of Ser. No. 195,630, Oct. 9, 1980, Pat. No. 4,335,009, which is a continuation-in-part of Ser. No. 160,788, Jun. 19, 1980, Pat. No. 4,287,084.

[51] Int. Cl.[3] .................... A61K 7/46

[52] U.S. Cl. .................... 252/522 R; 252/174.11; 568/385; 568/451; 568/893

[58] Field of Search .................... 252/522 R, 174.11; 568/385, 451, 893

[56] References Cited

U.S. PATENT DOCUMENTS

| | | | |
|---|---|---|---|
| 4,198,532 | 4/1980 | Ochsner | 252/522 R X |
| 4,304,689 | 12/1981 | Boden et al. | 252/522 R |
| 4,311,617 | 1/1982 | Ansari et al. | 252/522 R |
| 4,318,934 | 3/1982 | Boden | 426/534 |
| 4,321,255 | 3/1982 | Boden | 424/49 |

FOREIGN PATENT DOCUMENTS

| | | | |
|---|---|---|---|
| 2723636 | 12/1978 | Fed. Rep. of Germany | 252/522 R |
| 2001984 | 2/1979 | United Kingdom | 252/522 R |

OTHER PUBLICATIONS

Arctander, *Perfume and Flavor Chemicals*, vol. II, Monographs 2913, 2914, 2920, 3007 and 3008.

*Primary Examiner*—Thomas A. Waltz
*Attorney, Agent, or Firm*—Arthur L. Liberman

[57] ABSTRACT

Described are methods for augmenting or enhancing the aroma of perfumes and perfumed articles by adding thereto perfume aroma augmenting or enhancing quantities of novel methyl substituted-2-oxohexane derivatives produced by dimerizing isoamylene (2-methyl-2-butene); then oxidizing the resulting product using formic acid and hydrogen peroxide; then reducing the resulting ketone(s) with an alkali metal borohydride; and then, optionally, reacting the resulting alcohol(s) with acetic anhydride to form one or more esters; as well as perfume compositions, colognes and perfumed articles including solid or liquid anionic, cationic, nonionic or zwitterionic detergents, fabric softener compositions, hair preparations, perfumed polymers and deodorant compositions as well as bleaching compositions containing same.

Also covered is the genus of compounds defined according to the structure

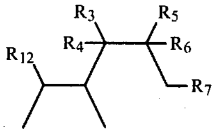

wherein $R_{12}$ represents hydroxyl:

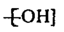

or acetoxy having the structure:

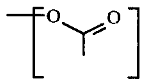

;

and wherein $R_3$, $R_4$, $R_5$, $R_6$ and $R_7$ represent hydrogen or methyl with the provisos that:

(i) the sum total of carbon atoms in $R_3$, $R_4$, $R_5$, $R_6$ and $R_7$ is three;
(ii) when $R_7$ is methyl, then $R_5$ and $R_6$ are both methyl, and
(iii) when either $R_3$ or $R_4$ is methyl, then $R_7$ is hydrogen.

6 Claims, 24 Drawing Figures

GLC PROFILE FOR EXAMPLE A.

GLC PROFILE FOR EXAMPLE A.

GLC PROFILE FOR EXAMPLE A.

GLC PROFILE FOR EXAMPLE A.
CRUDE PRODUCT

GLC PROFILE FOR EXAMPLE A.
DISTILLATION PRODUCT

FIG. 2A
NMR SPECTRUM FOR PEAK I OF EXAMPLE I, OF GLC OF FIG. 1E
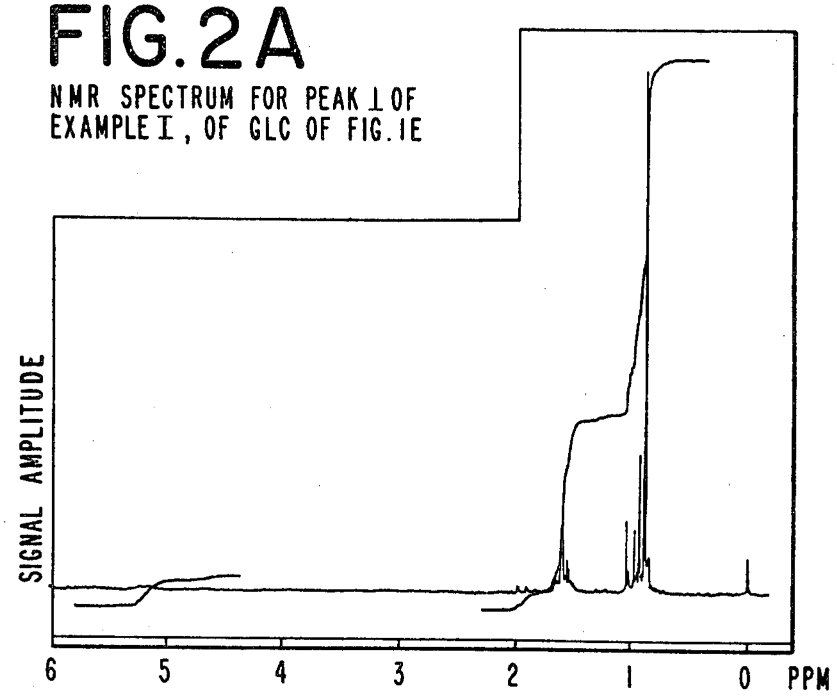
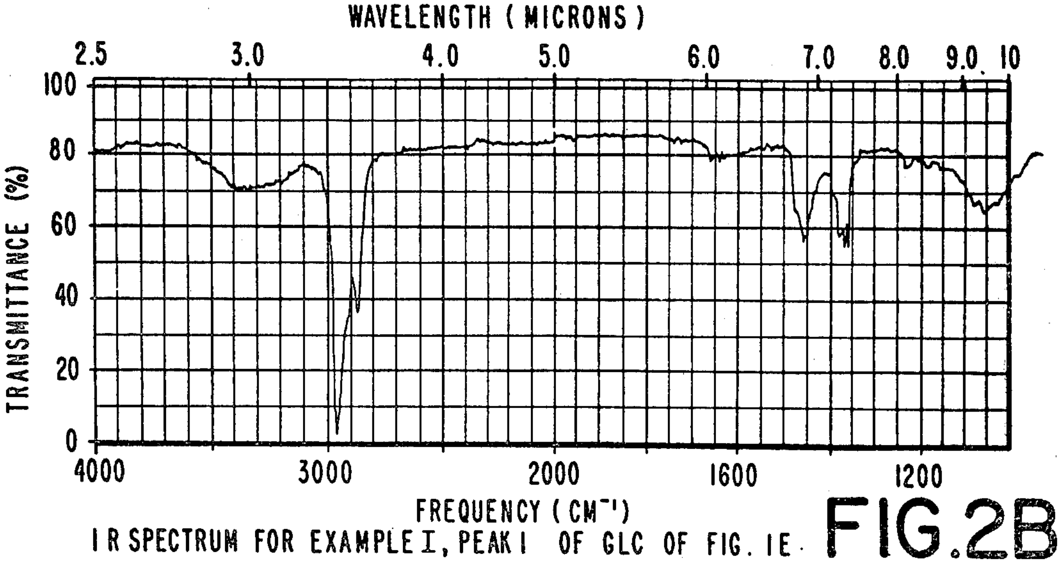
IR SPECTRUM FOR EXAMPLE I, PEAK I OF GLC OF FIG. 1E
FIG. 2B FIG. 3A
NMR SPECTRUM FOR EXAMPLE I, PEAK 2 OF GLC OF FIG. 1E
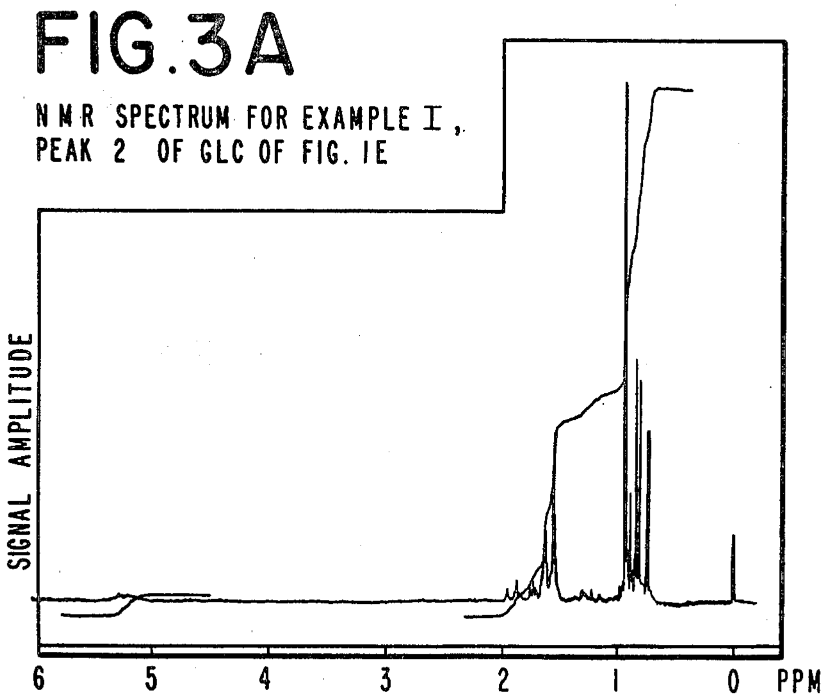
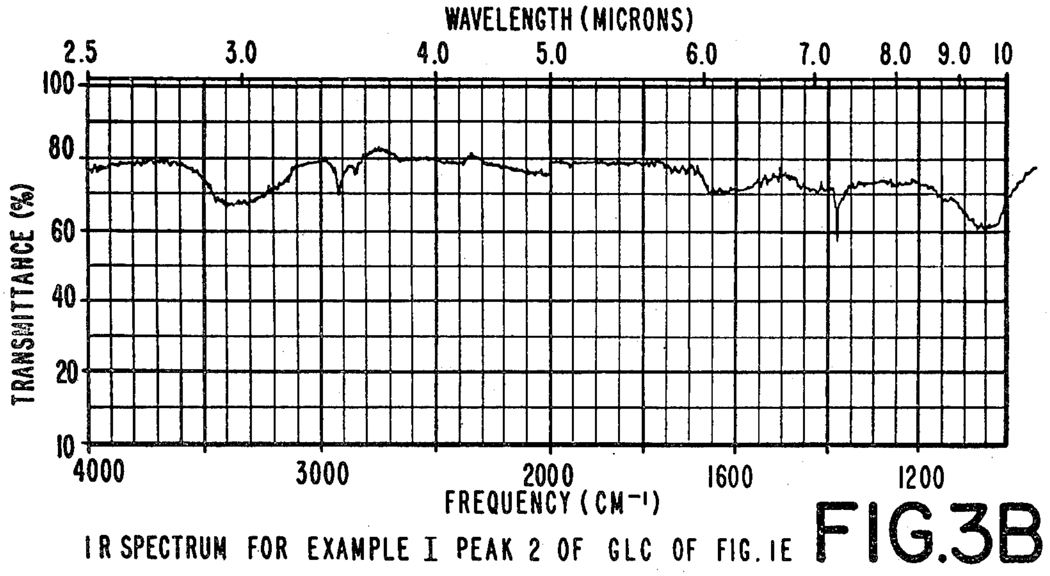
IR SPECTRUM FOR EXAMPLE I PEAK 2 OF GLC OF FIG. 1E
FIG. 3B

NMR SPECTRUM FOR PEAK 2 OF EXAMPLE I OF GLC OF FIG. 1B.

GLC PROFILE FOR EXAMPLE I.

NMR SPECTRUM FOR EXAMPLE I — PEAKS 31,32 & 33 OF FIG.5

I R SPECTRUM FOR EXAMPLE I — PEAKS 31,32 & 33 OF FIG. 5.

NMR SPECTRUM FOR EXAMPLE I — PEAKS 21, 22 & 23 OF FIG. 5.

I R SPECTRUM FOR EXAMPLE I – PEAKS 21, 22 & 23 OF FIG. 5.

GLC PROFILE FOR FRACTION I OF EXAMPLE II.

GLC PROFILE FOR EXAMPLE II. CRUDE

GLC PROFILE FOR EXAMPLE III

GLC PROFILE FOR EXAMPLE II, FRACTION 3.

GLC PROFILE FOR FRACTION 5 OF EXAMPLE II.

I R SPECTRUM FOR EXAMPLE III.

NMR SPECTRUM FOR EXAMPLE II.

NMR SPECTRUM FOR EXAMPLE III

I R SPECTRUM FOR EXAMPLE III.

METHYL SUBSTITUTED-2-OXOHEXANE DERIVATIVES AND PROCESS FOR PREPARING AND USING SAME

This application is a continuation-in-part of application for U.S. Letters Patent Ser. No. 195,630 filed on Oct. 9, 1980 now U.S. Pat. No. 4,335,009 issued on June 15, 1982 which, in turn, is a continuation-in-part of application for U.S. Letters Patent Ser. No. 160,788 filed on June 19, 1980, now U.S. Pat. No. 4,287,084 issued on Sept. 1, 1981.

BACKGROUND OF THE INVENTION

The instant invention provides methyl substituted-2-oxohexane derivatives and processes for preparing same as well as processes for using same for augmenting or enhancing the aroma of perfume compositions, colognes and perfumed articles. The methyl substituted-2-oxohexane derivatives of our invention are defined according to the structure:

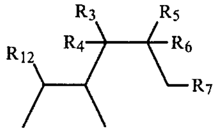

wherein $R_{12}$ represents hydroxyl having the structure:

or acetoxy having the structure:

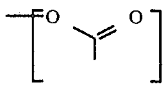

and wherein $R_3$, $R_4$, $R_5$, $R_6$ and $R_7$ each represent the same or different methyl or hydrogen with the provisos that:

(i) the sum total of the carbon atoms of $R_3$, $R_4$, $R_5$, $R_6$ and $R_7$ is three;

(ii) when $R_7$ is methyl, then $R_5$ and $R_6$ are each methyl; and (iii) when $R_7$ is hydrogen, then $R_3$ or $R_4$ is methyl.

Chemical compounds which can provide woody, camphoraceous, patchouli-like, fruity and amber-like aromas are highly desirable in the art of perfumery. Many of the natural materials which provide such fragrances and contribute such desired nuances to perfumery compositions and perfumed articles are high in cost, unobtainable at times, vary in quality from one batch to another and/or are generally subject to the usual variations in natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Application for U.S. Letters Patent Ser. No. 184,132 filed on Sept. 4, 1980 now U.S. Pat. No. 4,321,255 issued on Mar. 23, 1982 (incorporated by reference herein) discloses the production of unsaturated branched ketones according to the reaction:

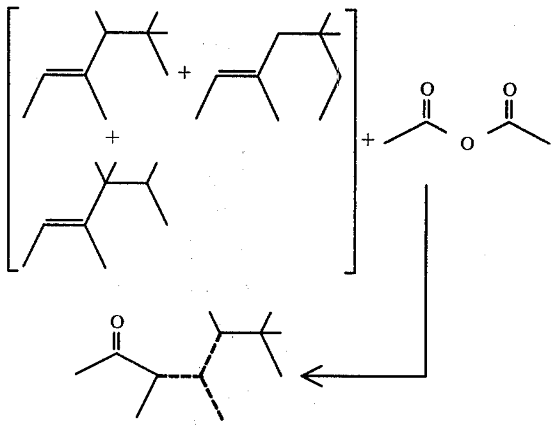

wherein in each of the structures containing dashed lines, these structures represent mixtures of molecules wherein in each of the molecules, one of the dashed lines represents a carbon-carbon double bond and each of the other of the dashed lines represent a carbon-carbon single bond. These compounds so produced are indicated to be useful for their organoleptic properties in augmenting or enhancing the aroma or taste of consumable articles including perfume compositions and colognes. It is noteworthy that the compounds defined according to the structure:

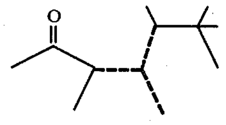

have unsaturation in the structure and, in addition, contain twelve carbon atoms rather than ten carbon atoms. Disclosure of the resulting alcohols produced by reaction of these ketones with methyl magnesium halide is set forth in application for U.S. Letters Patent Ser. No. 212,887 filed on Dec. 4, 1980 (now U.S. Pat. No. 4,318,934 issued on Mar. 9, 1982). The resulting alcohols have thirteen carbon atoms rather than the ten carbon atom containing alcohols of the instant application.

Nothing in the prior art discloses compounds defined according to the generic structure:

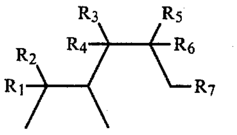

wherein $R_1$, $R_2$, $R_3$, $R_4$, $R_5$, $R_6$ and $R_7$ are defined supra.

"Diisoamylene" is indicated to be synthesized in the following references:

(i)—Murphy & Lane, Ind. Eng. Chem., Prod. Res. Dev., Vol. 14, No. 3, 1973, p. 167 (Title: Oligomerization of 2-Methyl-2-Butene in Sulfuric Acid and Sulfuric-Phosphoric Acid Mixtures).

(ii)—Whitmore & Mosher, Vol. 68, J. Am. Chem. Soc., February, 1946, p. 281 (Title: The Depolymerization of 3,4,5,5-Tetramethyl-2-Hexene and 3,5,5-Trimethyl-2-Heptene in Relation to the Dimerization of Isoamylenes).

(iii)—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv)—U.S. Pat. No. 3,627,700, issued on Dec. 14, 1971, (Zuech).

(v)—U.S. Pat. No. 3,538,181, issued on Nov. 3, 1970, (Banks).

(vi)—U.S. Pat. No. 3,461,184 issued on Aug. 12, 1969 (Hay, et al).

(vii)—Tausz, Chemische Zentralblatt, 1919, II, 125, (Production of Di-isoamylene From Isoamylene Using Mercury Acetate Catalyst).

United Kingdom Pat. No. 796,130 published on June 4, 1958 discloses the synthesis of polyalkylindanes by means of, interalia, reacting alpha-methylstyrene with trimethylethene (2-methyl-butene-2) in the presence of an acid catalyst such as sulfuric acid or boron trifluoride methyletherate. It is further indicated that such compounds are useful intermediates in the production of perfumery compounds. Apparently, however, the more volatile diisoamylenes produced as side-products in the reaction of 2-methyl-butene-2 with alpha-methylstyrene are discarded.

The diisoamylene useful as a starting material in the instant case may be distilled from the reaction product (as see Example A infra) at a temperature in the range of 36°-40° C.; a liquid temperature in the range of 74°-94° C. and a pressure of 4-5 mm/Hg.

BRIEF DESCRIPTION OF THE DRAWINGS

FIG. 2A represents the NMR spectrum for Peak 1 of the GLC profile of FIG. 1E.

FIG. 2B represents the infra-red spectrum for Peak 1 of the GLC profile of FIG. 1E.

FIG. 3A represents the NMR spectrum for Peak 2 of the GLC profile of FIG. 1E.

FIG. 3B represents the infra-red spectrum for Peak 2 of the GLC profile of FIG. 1E.

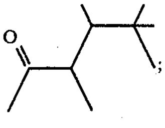;
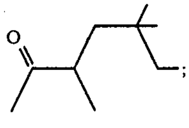;
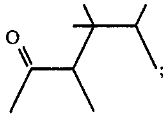;
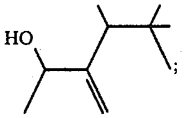;
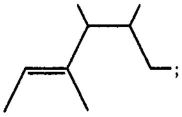;
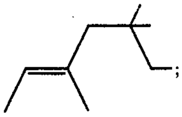;
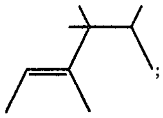;
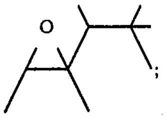;
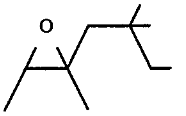 and 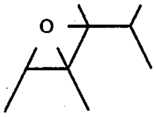

Figure 5:
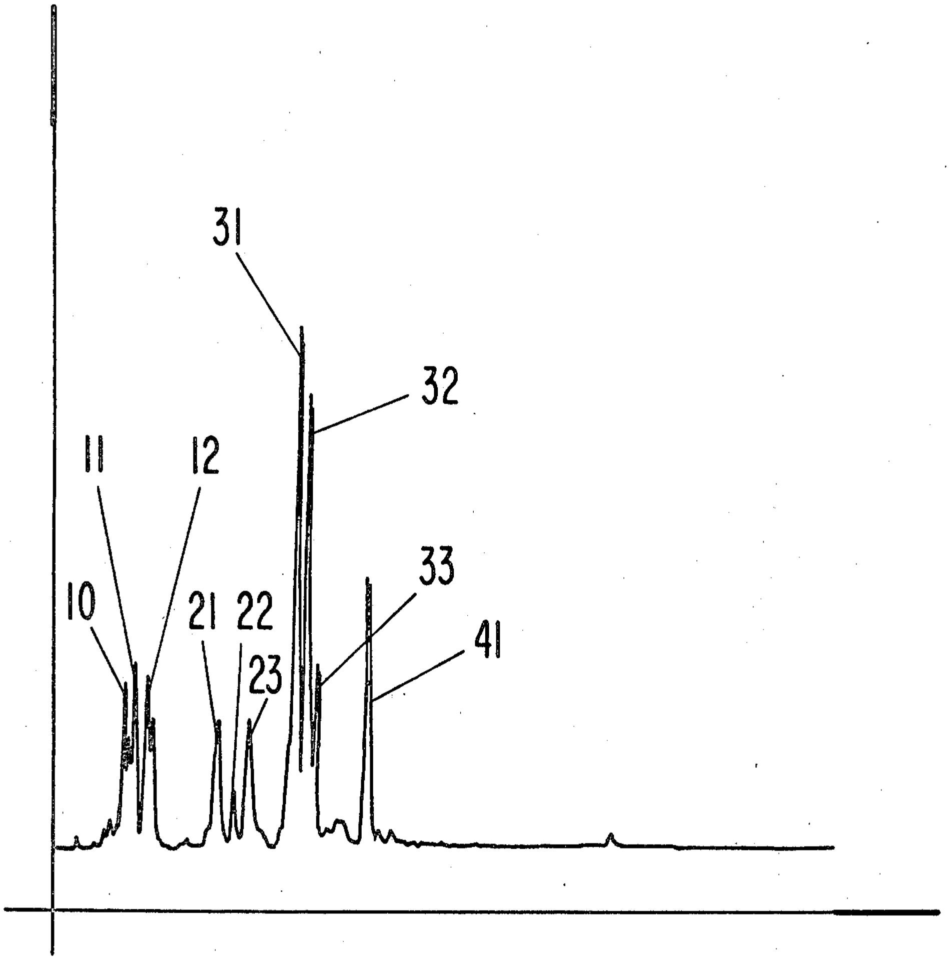
FIG. 5 is the GLC profile for the reaction product of Example I containing the compounds having the structures.
Figure 6:
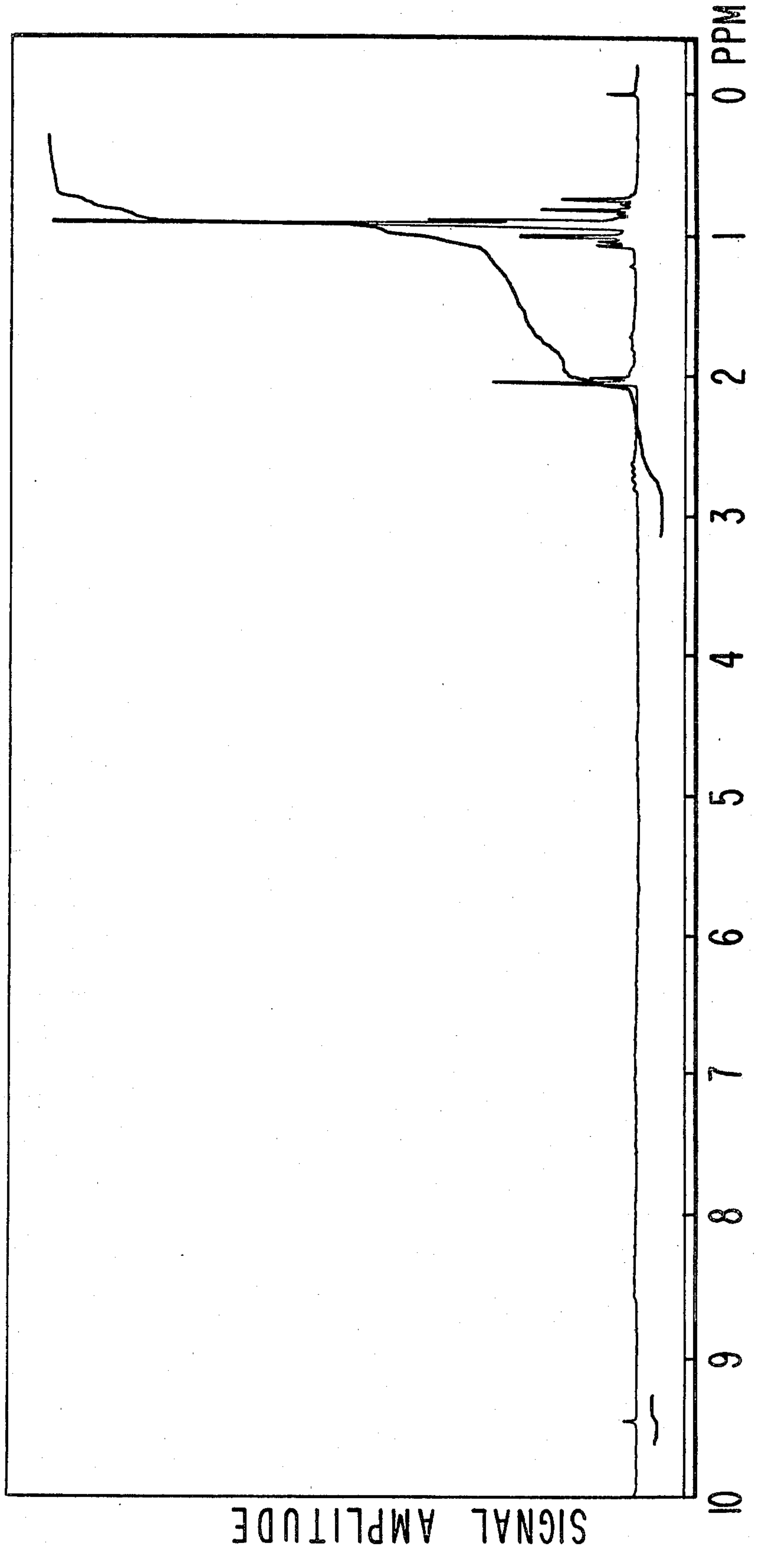

FIG. 6 is the NMR spectrum for Peaks 31, 32 and 33 of the GLC profile of FIG. 5 containing the compounds having the structures:

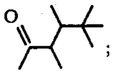; 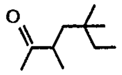 and 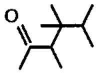

Figure 7:
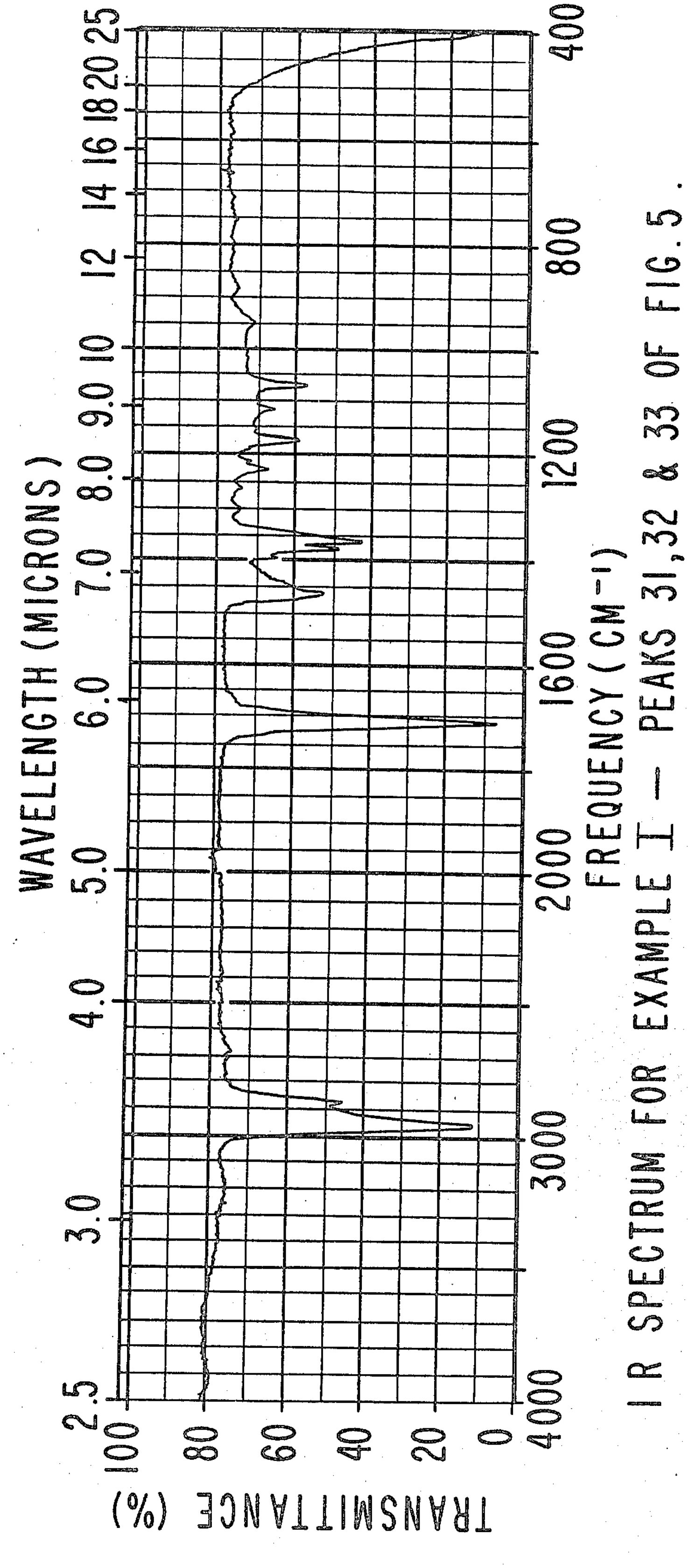

FIG. 7 is the infra-red spectrum for Peaks 31, 32 and 33 of FIG. 5, the GLC profile of the reaction product of Example I containing the compounds having the structures:

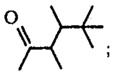; 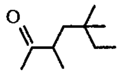 and 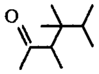

Figure 8:
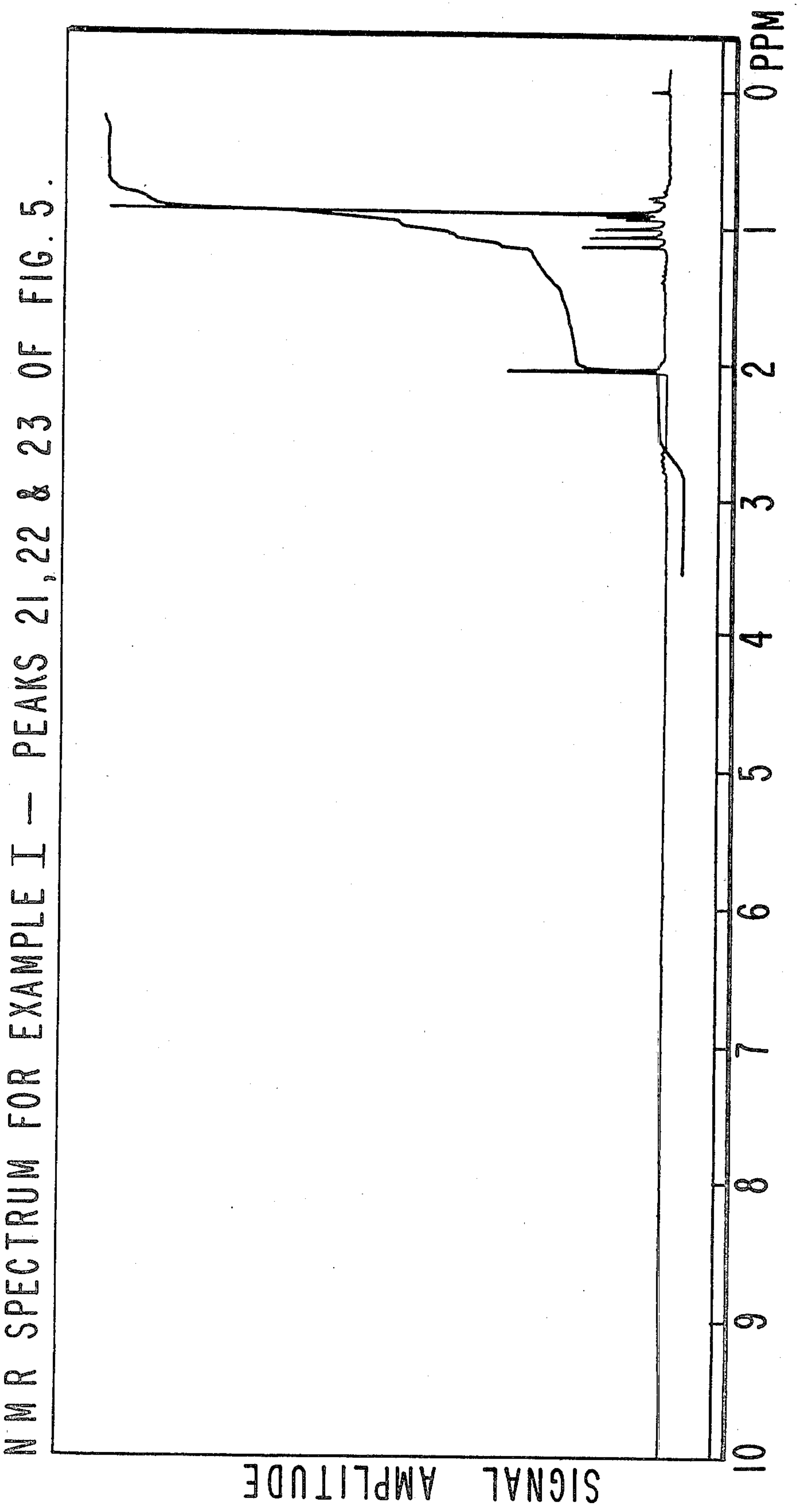

FIG. 8 is the NMR spectrum for Peaks 21, 22 and 23 of FIG. 5, the GLC profile of the reaction product of Example I containing the compounds having the structures:

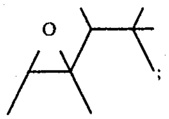; 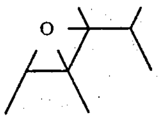 and 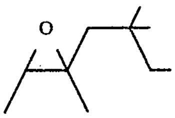

Figure 9:
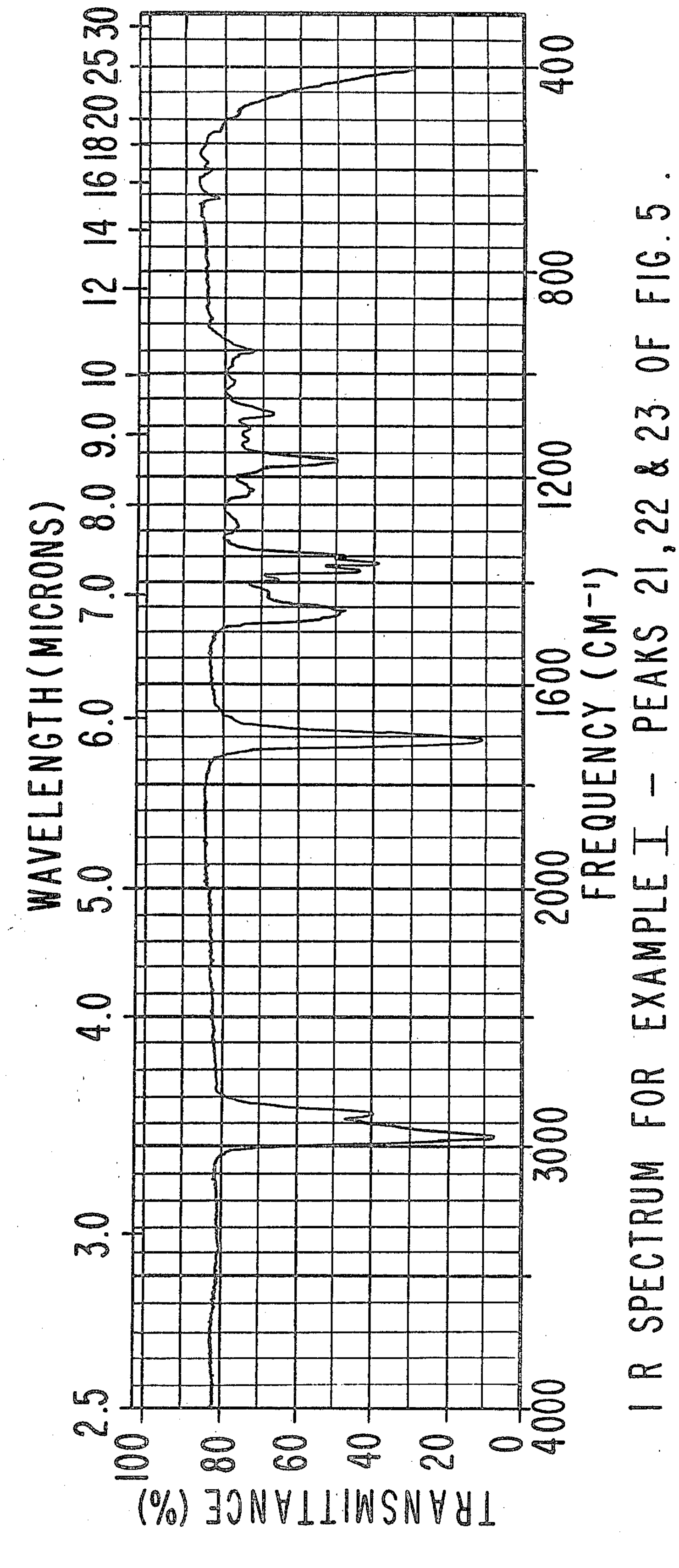

FIG. 9 is the infra-red spectrum for Peaks 21, 22 and 23 of the GLC profile of FIG. 5 which is the GLC profile of the reaction product of Example I containing the compounds having the structures:

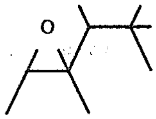
;
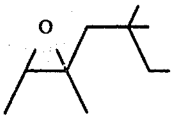
and
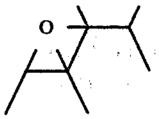

Figure 10:
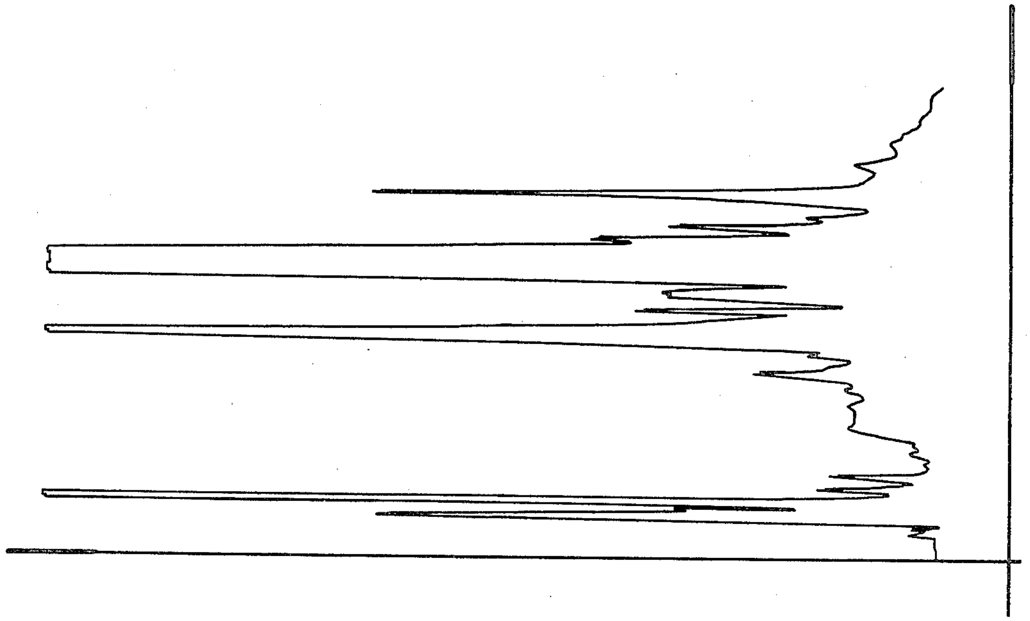

FIG. 10 is the GLC profile from the crude reaction product prior to distillation (conditions: 10'×¼" column Carbowax 68; programmed at 100°-220° C. at 8° C. per minute). The reaction product of Example II contains a mixture of compounds defined according to the structures:

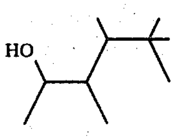
;
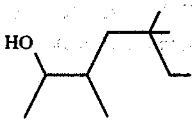
and
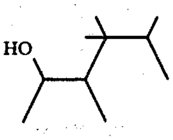

Figure 11:
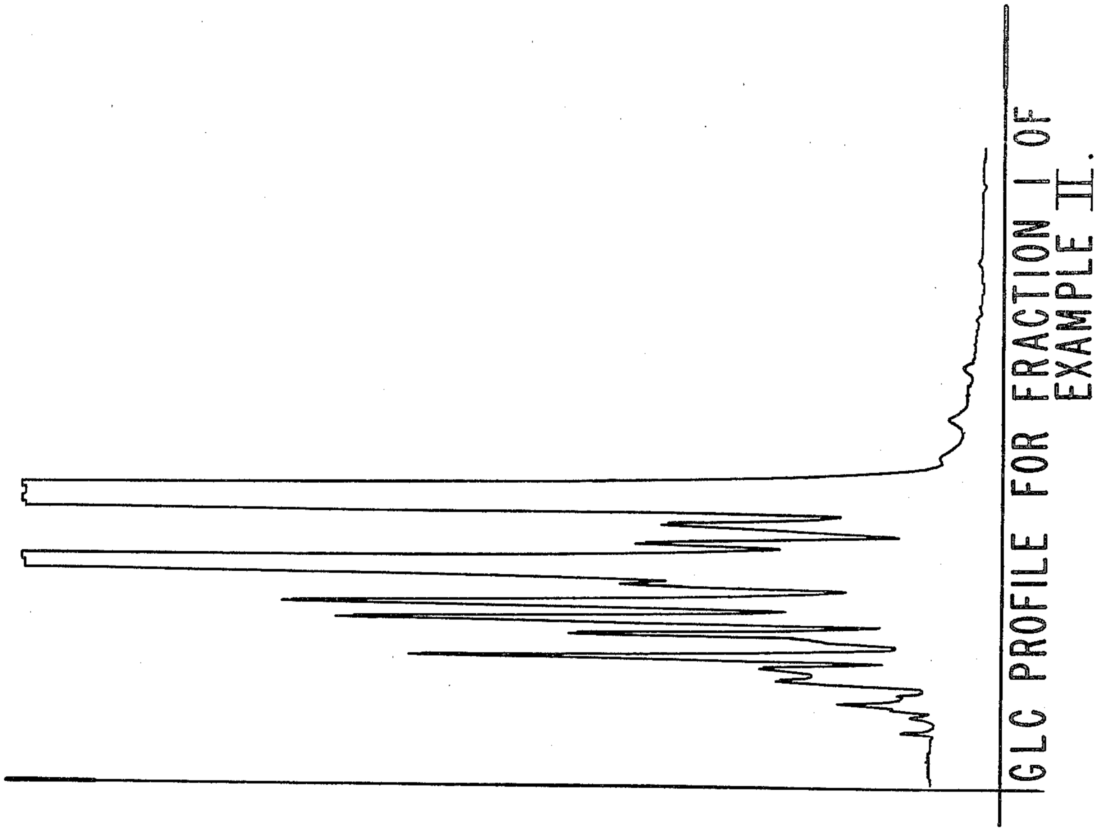

FIG. 11 is the GLC profile of fraction 1 of the distillation product of the reaction product of Example II containing the compounds having the structures:

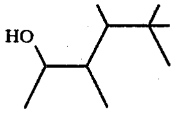
;
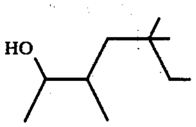
and
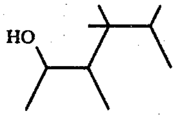

Figure 12:
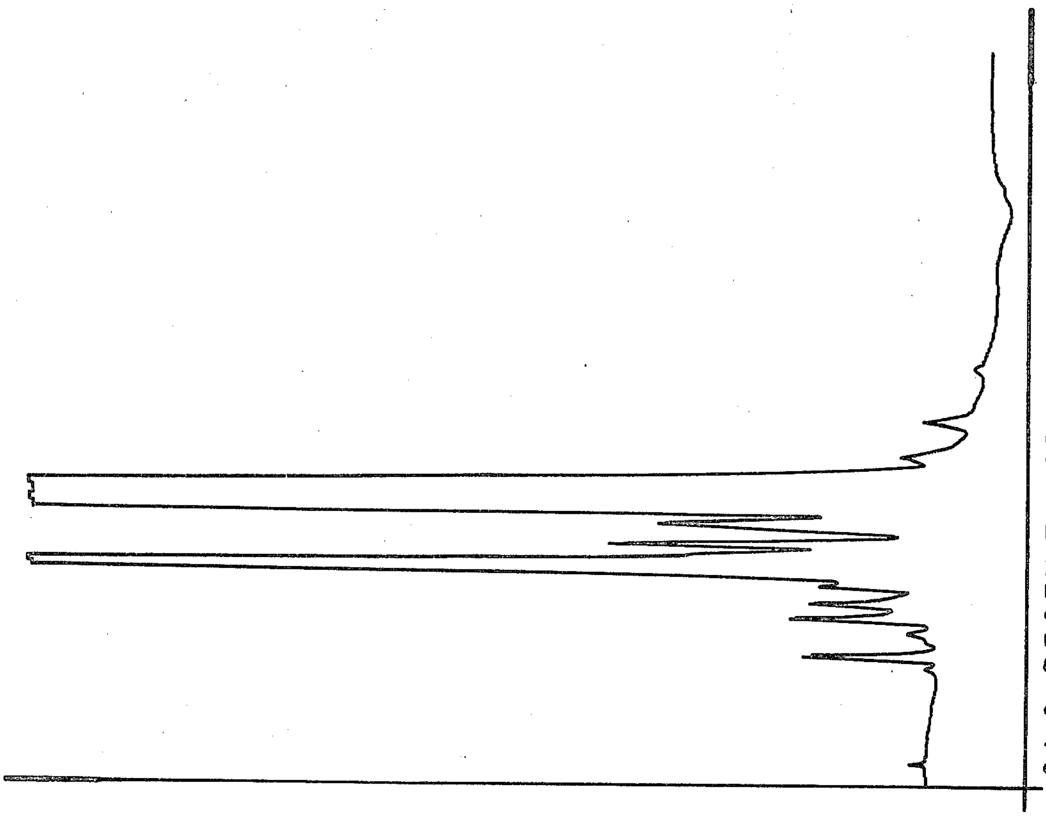

FIG. 12 is the GLC profile for fraction 3 of the distillation product of the reaction product of Example II containing the compounds having the structures:

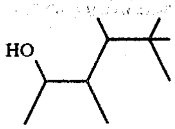
;
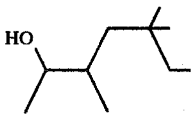
and
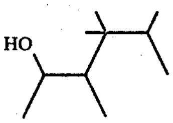

Figure 13:
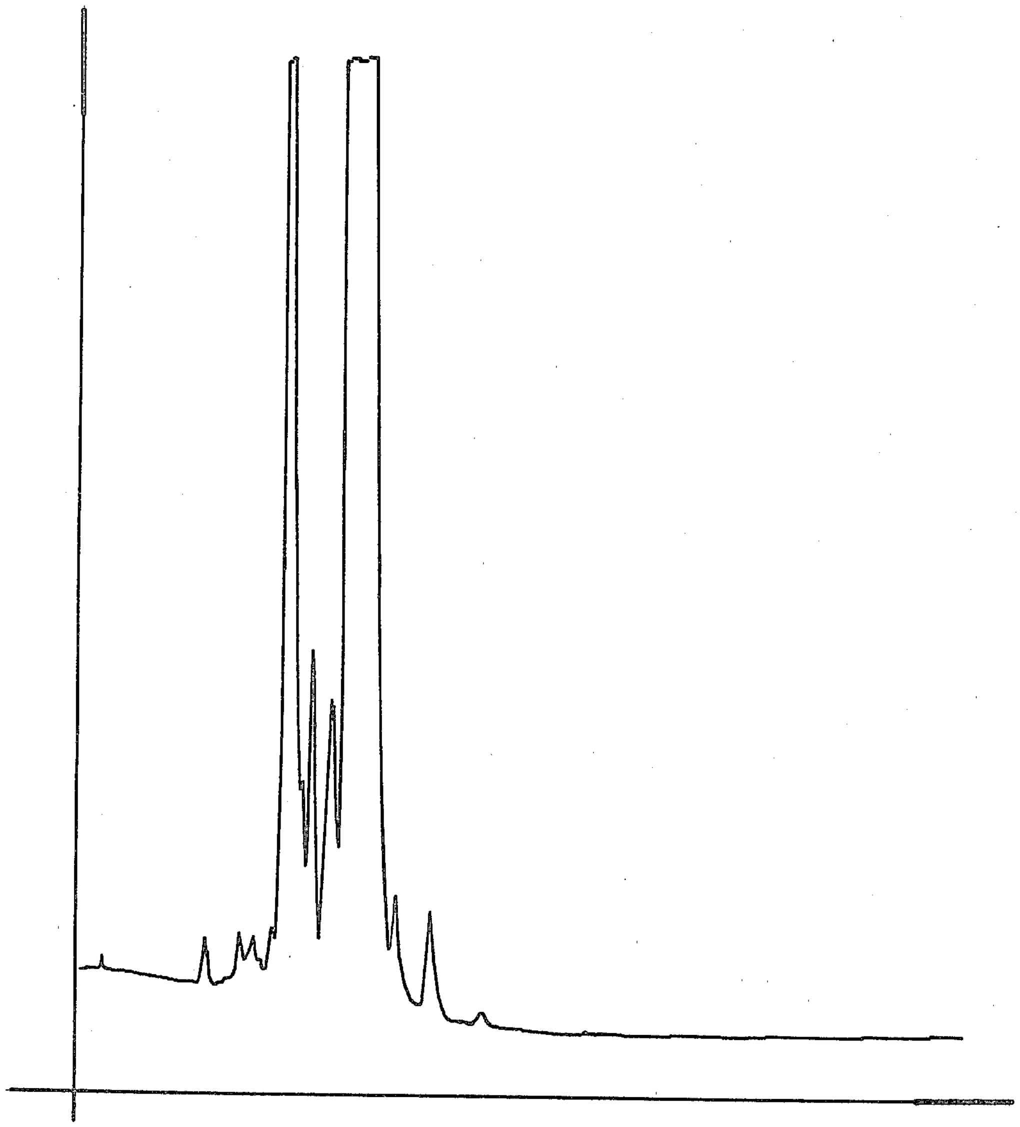

FIG. 13 is the GLC profile for fraction 5 of the distillation product of the reaction product of Example II containing the compounds having the structures:

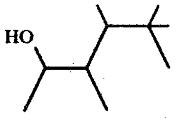
;
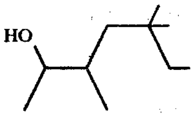
and
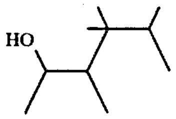

Figure 14:
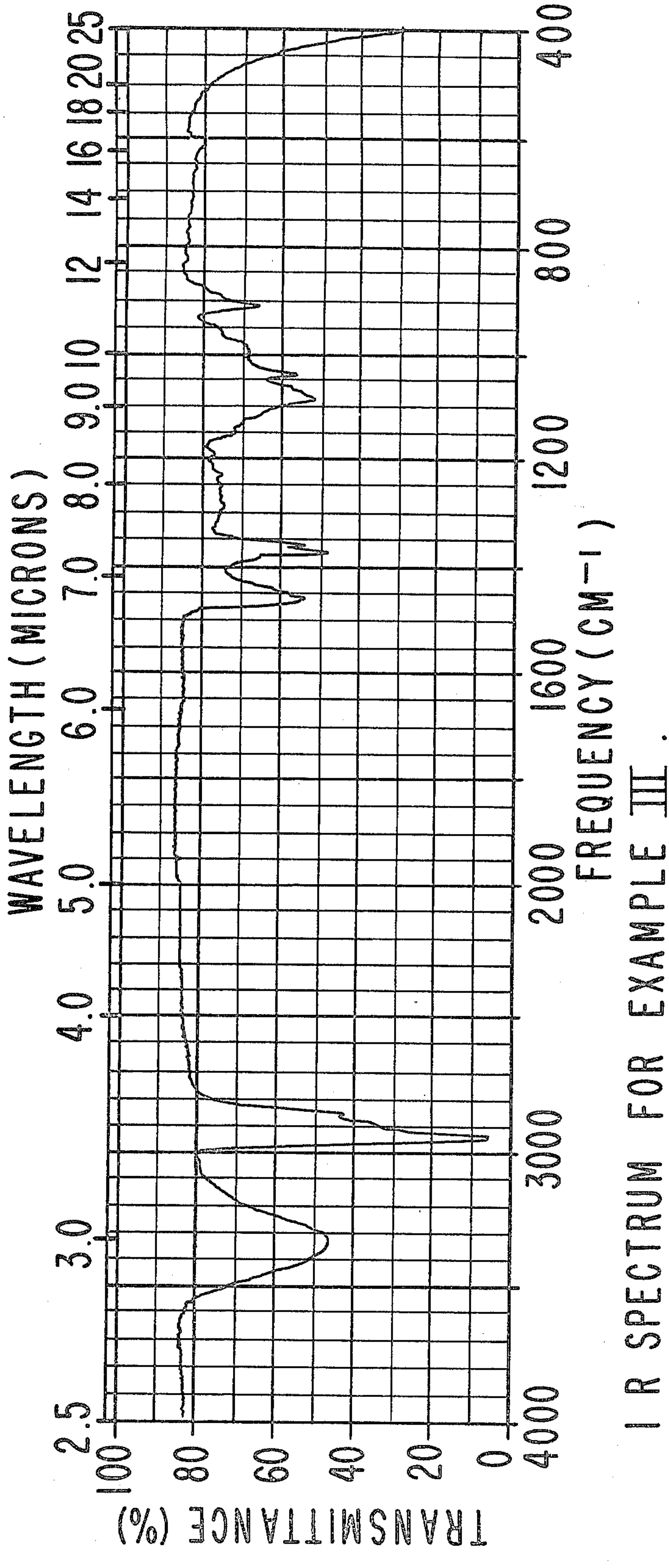

FIG. 14 is the infra-red spectrum for the distillation product of the reaction product of Example II containing the compounds having the structures:

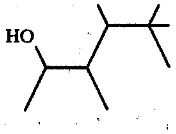
;
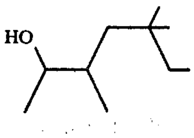
and
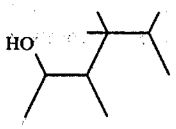

Figure 15:
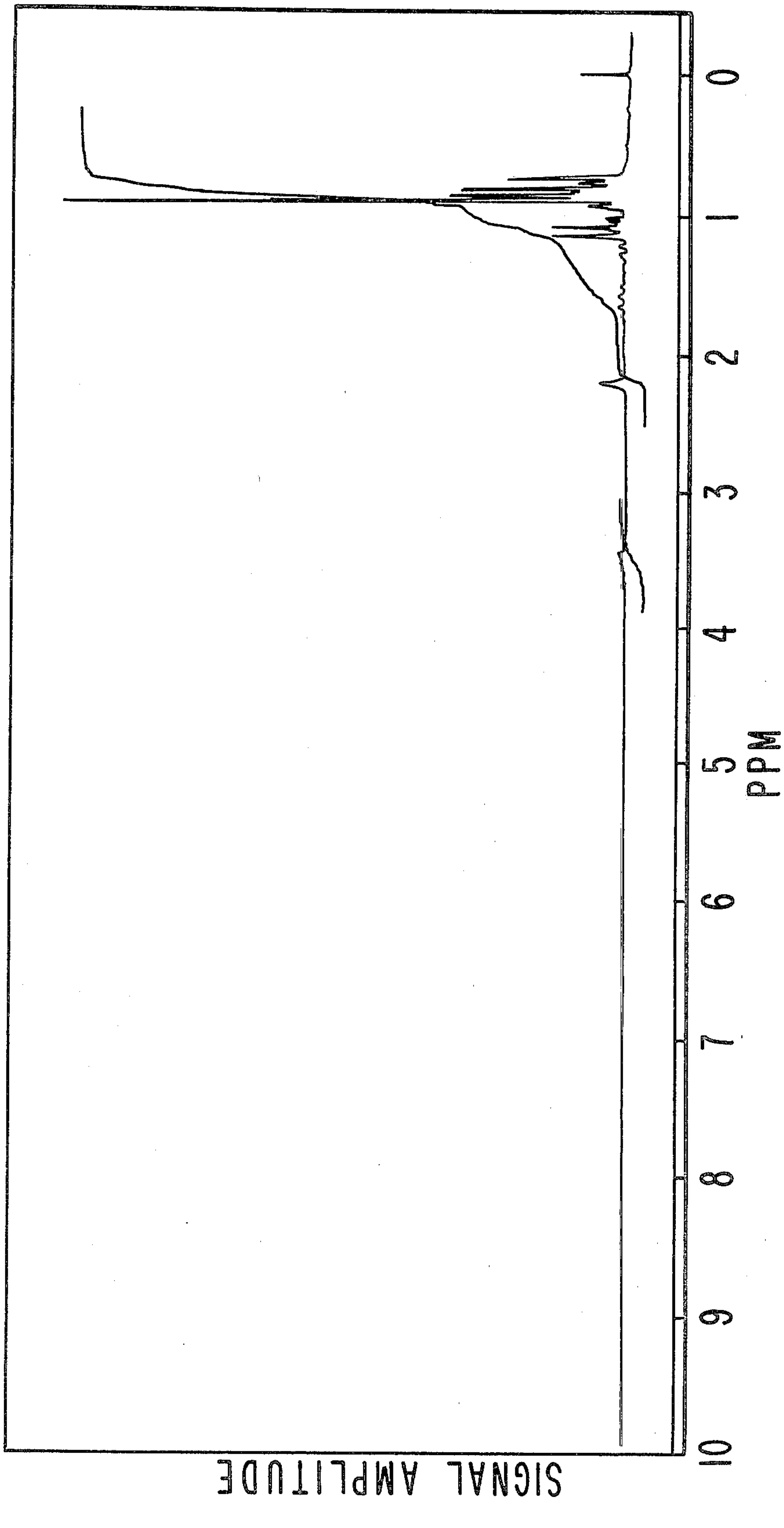

FIG. 15 is the NMR spectrum for the distillation product of the reaction product of Example II containing the compounds having the structures:

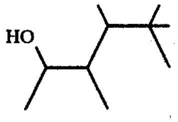
;
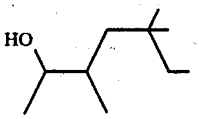
and
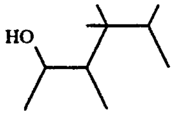

Figure 16:
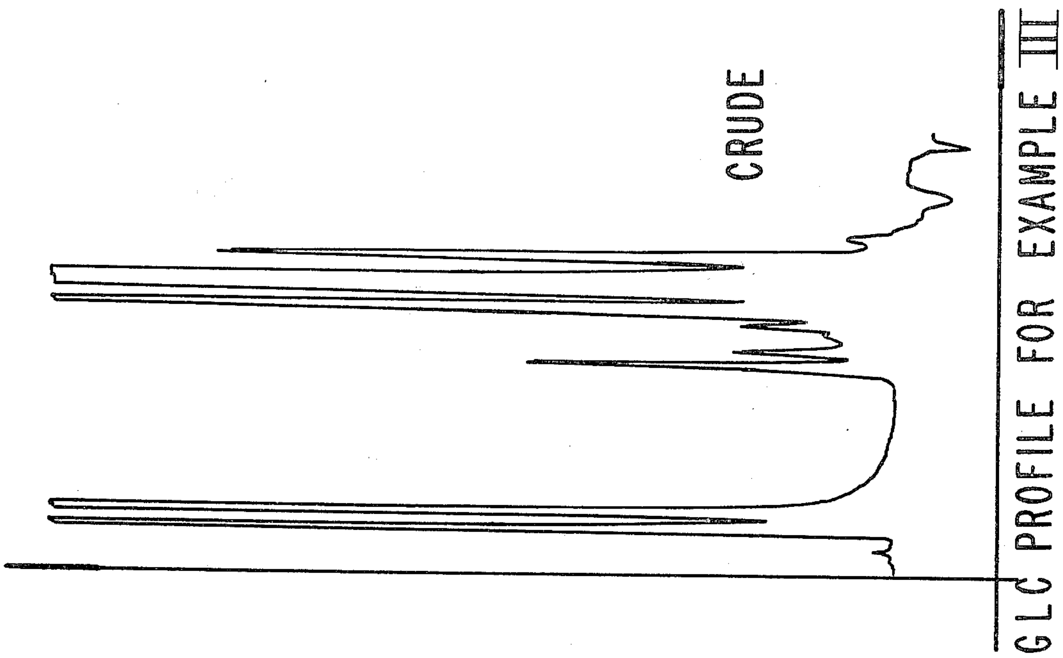

FIG. 16 is the GLC profile for the crude reaction product of Example III containing the compounds having the structures:

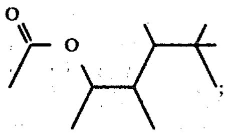
;
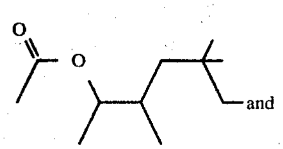
and
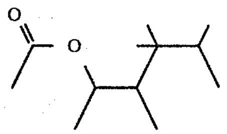

Figure 17:
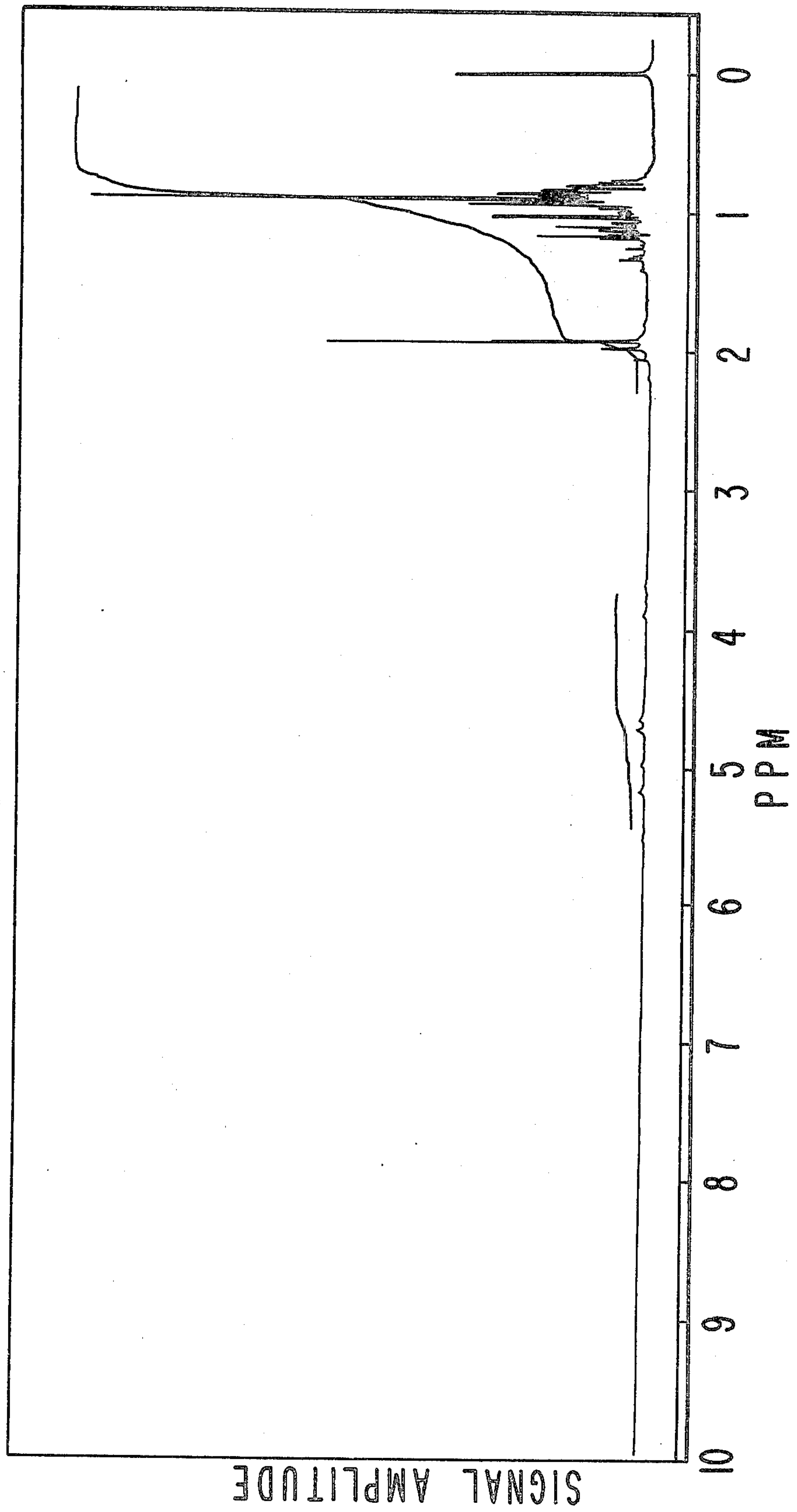

FIG. 17 is the NMR spectrum for the distillation product of the reaction product of Example III containing the compounds having the structures:

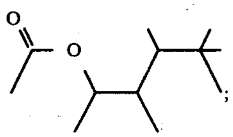
;

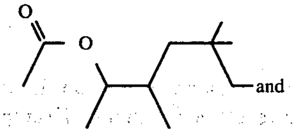
and

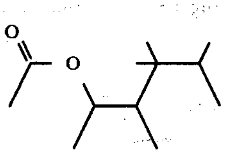

Figure 18:
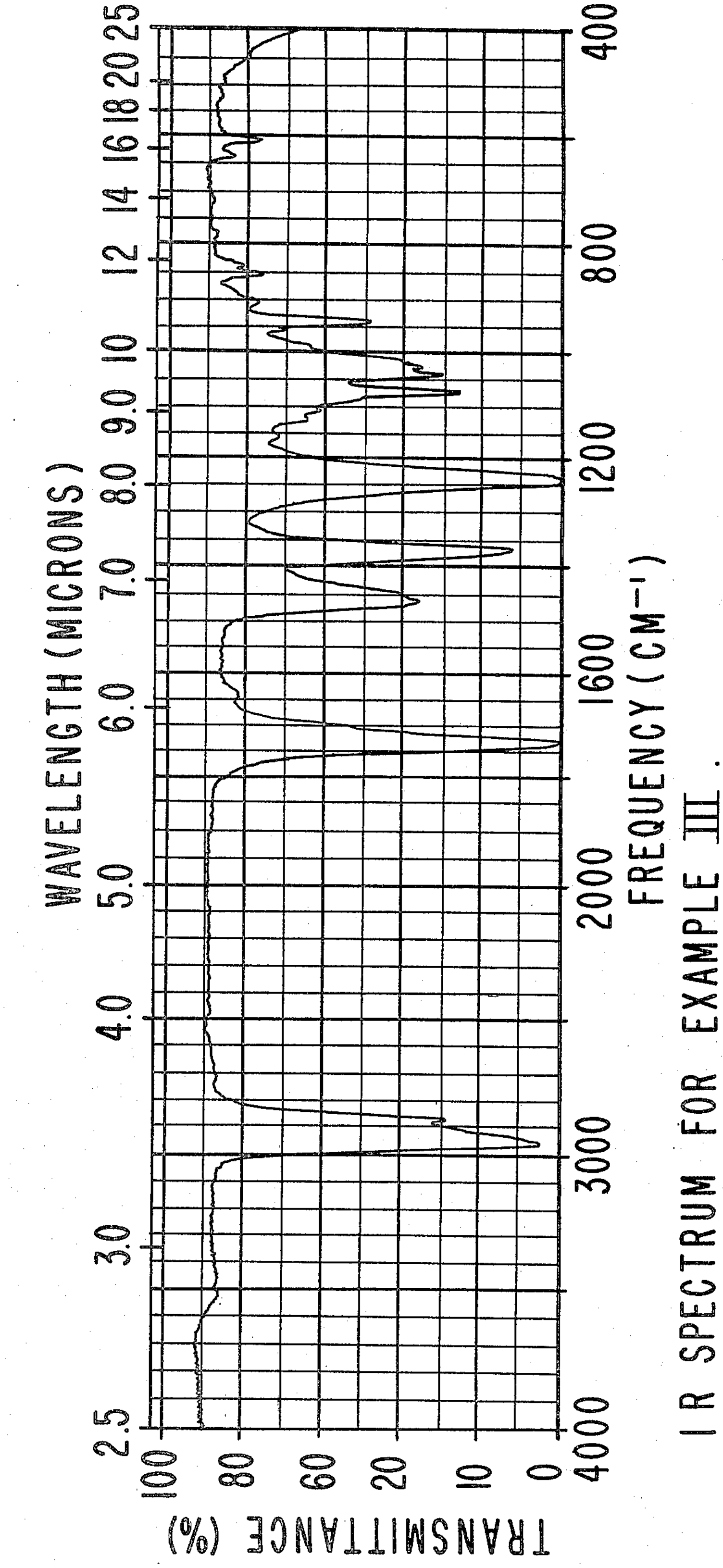

FIG. 18 is the infra-red spectrum for the distillation product of the reaction product of Example III containing the compounds having the structures:

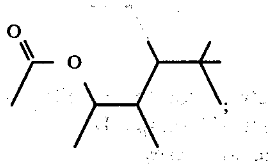
;

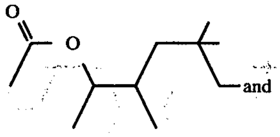
and

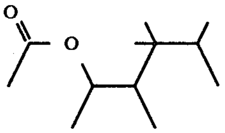

DETAILED DESCRIPTION OF THE DRAWINGS

Figure 1A:
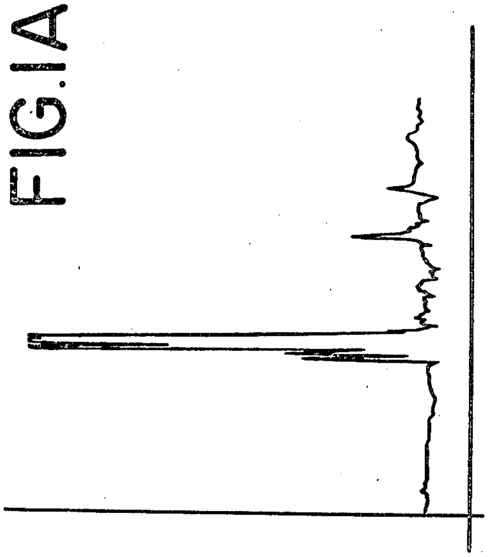
FIG. 1A represents the GLC profile for the reaction product of Example A using a 70% sulfuric acid catalyst at 35° C., wherein diisoamylene is produced by dimerizing isoamylene.
Figure 1B:
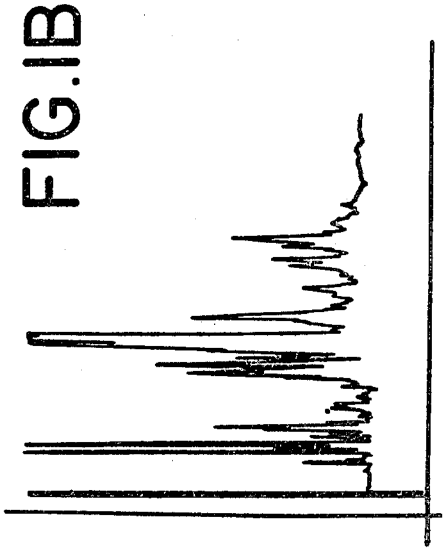
FIG. 1B represents the GLC profile for the reaction product of Example A using the Amberlyst ®15 acidic ion exchange resin catalyst at a temperature of 150° C. wherein isoamylene is dimerized to produce diisoamylene.
Figure 1C:
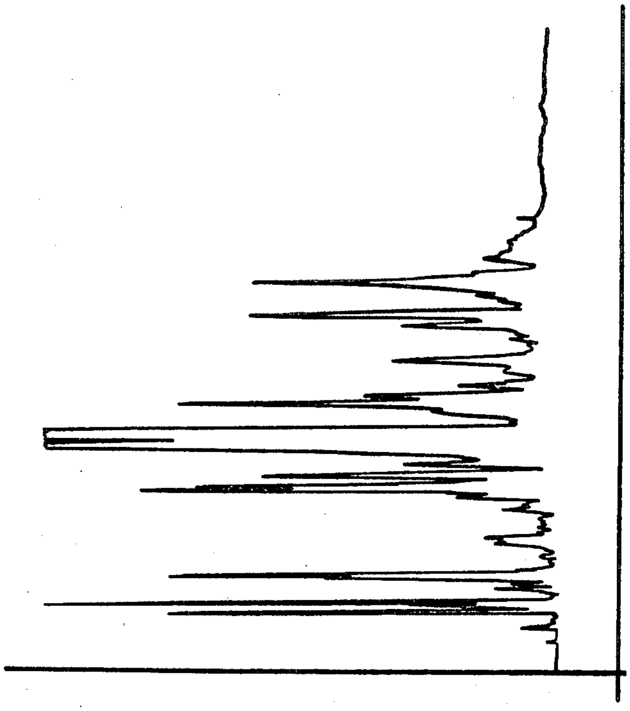
FIG. 1C represents the GLC profile for the reaction product of Example A using an Amberlyst ®15 catalyst at 100° C. wherein isoamylene is dimerized to produce diisoamylene.
Figure 1D:
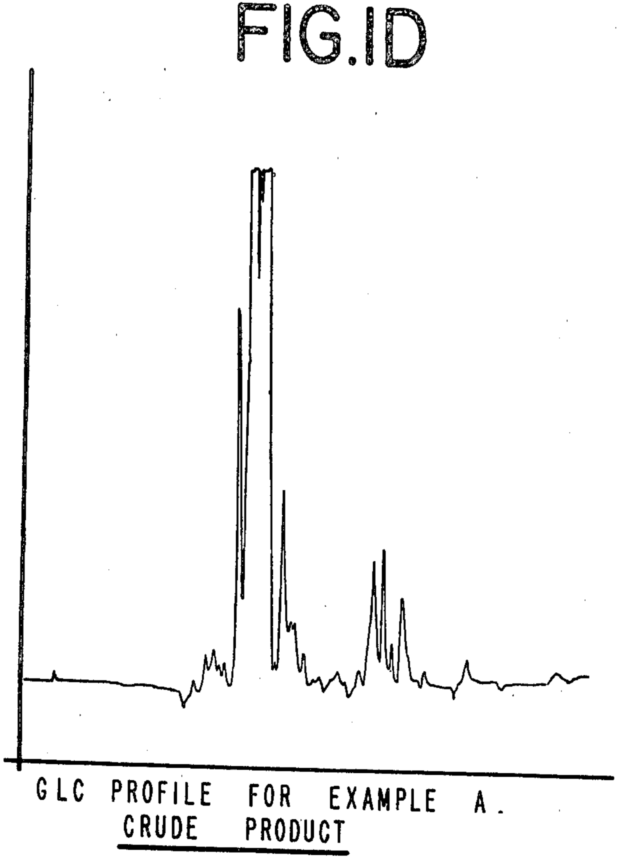
FIG. 1D represents the GLC profile for the reaction product of Example A using a sulfuric acid catalyst and an alpha-methylstyrene diluent at 35° C. according to the conditions of United Kingdom Patent Specification No. 796,130 (crude reaction product) wherein isoamylene is dimerized to produce diisoamylene.
Figure 1E:
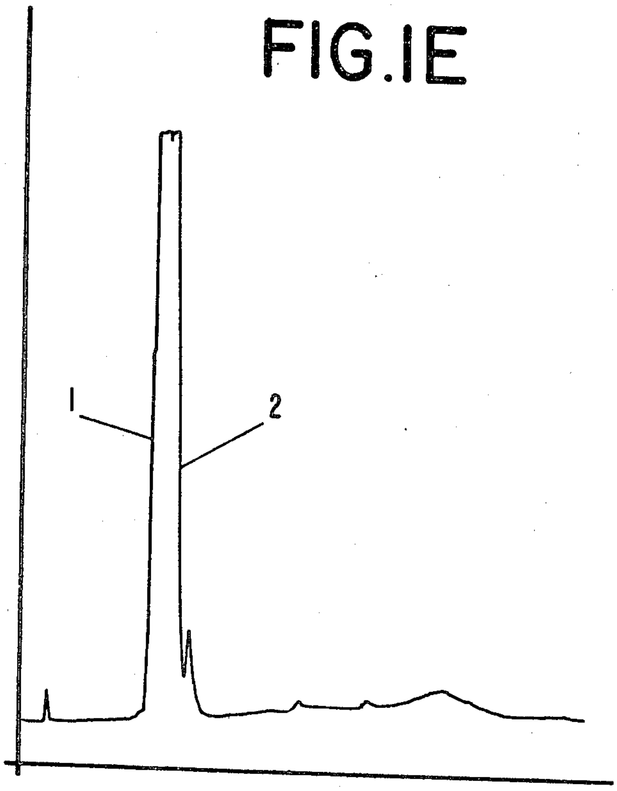
FIG. 1E represents the GLC profile for the reaction product of Example A using a sulfuric acid catalyst at 35° C. and an alpha-methylstyrene diluent according to the conditions of United Kingdom Patent Specification 796,130 (distilled reaction product) wherein isoamylene is dimerized to produce diisoamylene. The distillation range of the diisoamylene thus produced is as follows: vapor temperature 36°-40° C.; liquid temperature 74°-94° C.; and pressure 4-5 mm/Hg.

FIG. 1E is the GLC profile for the reaction product of Example A-1 wherein in dimerizing isoamylene to form diisoamylene, sulfuric acid catalyst is used at a temperature of 35° C. and an alpha-methyl styrene diluent is used according to the conditions of United Kingdom Patent Specification No. 796,130. The distillation range for the diisoamylene is 36°–40° C. vapor temperature and 74°–94° C. liquid temperature and a pressure of 4–5 mm/Hg. The Peak indicated by reference numeral "1" and reference numeral "2" are peaks signifying one of the isomers:

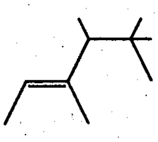
and/or
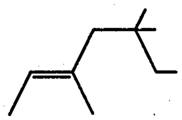

with the isomer having the structure:

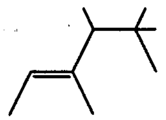

being the most prevalent of the three isomers having the structures:

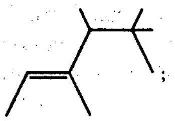
;
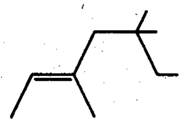
and
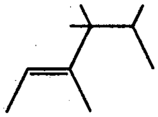

FIG. 5 is the GLC profile for the reaction product of Example I. In FIG. 5, the Peaks indicated by reference numerals "10", "11" and "12" are for the "starting material", the diisoamylene peaks having the structures:

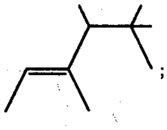
;
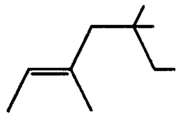
and
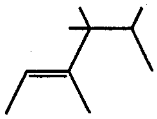

The Peaks indicated by reference numerals "21", "22" and "23" are those for the epoxy compounds created as a result of the oxidation having the structures:

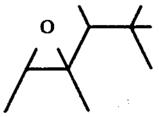
;
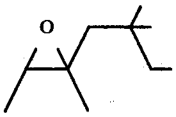
and
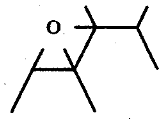

The Peaks in FIG. 5 indicated by reference numerals "31", "32" and "33" are those for the saturated branched ketones having the structures:

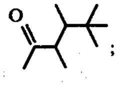
;
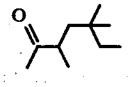
and
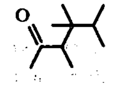

Peak 41 in FIG. 5 is the Peak which signifies the unsaturated alcohol defined according to the structure:

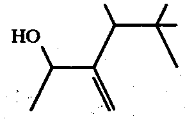

THE INVENTION

It has now been determined that certain methyl substituted oxohexane derivatives defined according to the structure:

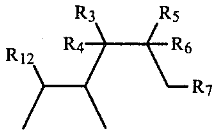

wherein $R_{12}$ represents hydroxyl having the structure:

or acetoxy having the structure:

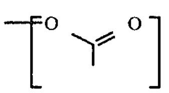

and wherein $R_3$, $R_4$, $R_5$, $R_6$ and $R_7$ represent the same or different hydrogen or methyl with the provisos that:

(i) when $R_7$ is methyl, then $R_5$ and $R_6$ are each methyl;

(ii) the sum total of carbon atoms in $R_3$, $R_4$, $R_5$, $R_6$ and $R_7$ is three; and (iii) when $R_7$ is hydrogen, then $R_3$ or $R_4$ is methyl, are capable of imparting or augmenting or enhancing a variety of fragrances in or to consumable materials.

Briefly, our invention contemplates augmenting or enhancing fragrances of such consumable materials as perfumes, perfumed articles (e.g. solid or liquid anionic, cationic, nonionic or zwitterionic detergents, cosmetic powders, fabric softener compositions, fabric softener articles, hair conditioners, perfumed plastics and floor waxes) and colognes by adding thereto a small but effective amount of at least one of the compounds defined according to one of the structures:

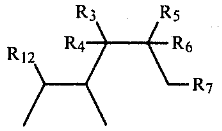

wherein $R_{12}$, $R_3$, $R_4$, $R_5$, $R_6$ and $R_7$ are defined supra or represented individually by the compounds:

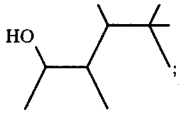
;
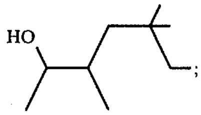
;
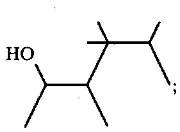
;
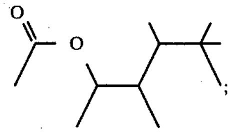
;
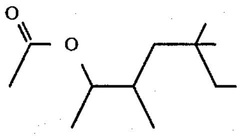
and
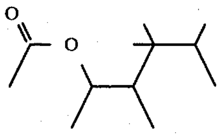

The foregoing compounds will hereinafter be indicated herein to be "methyl substituted oxohexane derivatives" of our invention.

The methyl substituted oxohexane derivatives of our invention augment or enhance woody, camphoraceous, patchouli-like, fruity and amber-like aromas of perfumes, perfumed articles and colognes thereby causing one or more of said methyl substituted oxohexane derivatives of our invention to be useful particularly in "eucalyptus" type fragrances. Furthermore, the methyl substituted oxohexane derivatives of our invention have unobvious and unexpected stability particularly in the presence of strong oxidizing agents such as hypochlorite bleach solutions. Thus, the methyl substituted oxohexane derivatives of our invention can be used particularly to augment or enhance the aroma of perfumed bleach compositions particularly perfumed hypochlorite bleach compositions.

The methyl substituted oxohexane derivatives of our invention defined according to the structure:

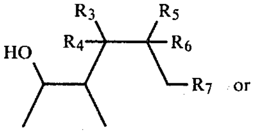
or
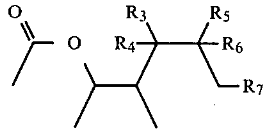

wherein $R_3$, $R_4$, $R_5$, $R_6$ and $R_7$ are defined supra, may be prepared by (i) first reacting 2-methyl-2-butene in the presence of an acidic catalyst which may be a Lewis acid such as zinc chloride, aluminum chloride, aluminum bromide, diethyl aluminum chloride, diethyl aluminum bromide, ethyl dialuminum chloride and ethyl dialuminum bromide, boron trifluoride, boron trifluoride etherate or any other catalyst enumerated in the following references:

(i)—Murphy & Lane, Ind. Eng. CHem., Prod. Res. Dev., Vol. 14, No. 3, 1975, p. 167 (Title: Oligomerization of 2-Methyl-2-Butene in Sulfuric Acid and Sulfuric-Phosphoric Acid Mixtures).

(ii)—Whitmore & Mosher, Vol. 68, J. Am. Chem. Soc., February, 1946, p. 281 (Title: The Depolymerization of 3,4,5,5-Tetramethyl-2-Hexene and 3,5,5-Trimethyl-2-Heptene in Relation to the Dimerization of Isoamylenes).

(iii)—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv)—U.S. Pat. No. 3,627,700, issued on Dec. 4, 1971, (Zuech).

(v)—U.S. Pat. No. 3,538,181, issued on Nov. 3, 1970, (Banks).

(vi)—U.S. Pat. No. 3,461,184 issued on Aug. 12, 1969 (Hay, et al).

(vii)—Tausz, Chemische Zentralblatt, 1919, II, 125 (Production of Di-isoamylene From Isoamylene Using Mercury Acetate Catalyst).

thereby forming the compounds having the structures:

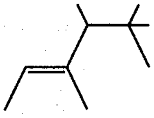
;
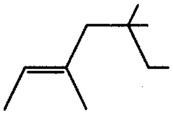
and
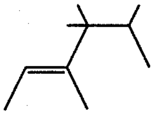

(ii) then, one or more of the compounds having the structures:

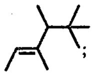; 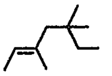 and/or 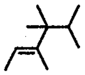

is then oxidized using a formic acid/concentrated hydrogen peroxide reagent according to the reaction:

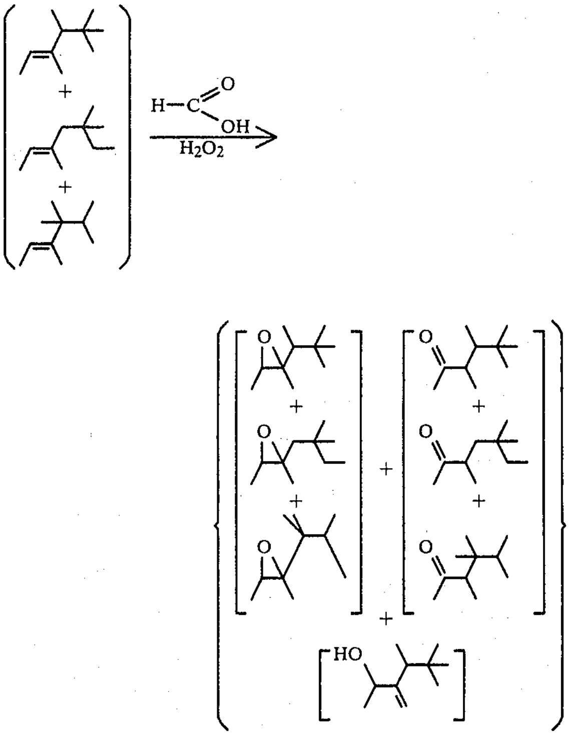

It is preferred that the concentration of diisoamylene: formic acid be between 1:1 and about 3:1 and the mole ratio of diisoamylene:hydrogen peroxide be between about 1:1 up to about 4:1 moles diisoamylene:moles hydrogen peroxide.

It is preferred that the concentration of hydrogen peroxide be in the range of from about 30% up to about 55% with a preferred concentration (weight:weight in water) of hydrogen peroxide being about 50%. Too low a concentration of hydrogen peroxide will not cause the proper reaction to be effected and too high a concentration of hydrogen peroxide is dangerous to use.

It is preferred that the reaction temperature be in the range of from about 45° C. up to about 75° C. with the most preferred range being from 50° up to 70° C. Higher temperatures of reaction give rise to shorter periods of time but less controllable reactions. Thus, at 50° C. the reaction time using a 50% hydrogen peroxide solution in 4.5 hours.

At the end of the reaction, the reaction mass is neutralized whereby any excess hydrogen peroxide is removed from the reaction mass. The reaction mass is then neutralized, e.g. using saturated sodium chloride solution, and then distilled whereby the desired fractions containing the ketones having the structures:

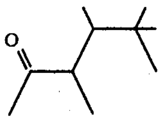; 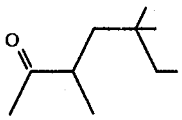 and 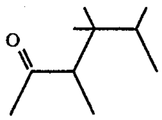

are removed at a vapor temperature of 95°–100° C.; a liquid temperature of 109°–120° C. and a pressure of 50 mm/Hg.

One or more of the resulting ketones defined according to the structures:

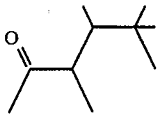; 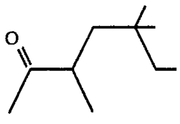 and 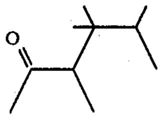

is then reduced using an alkali metal borohydride reducing agent according to the reaction:

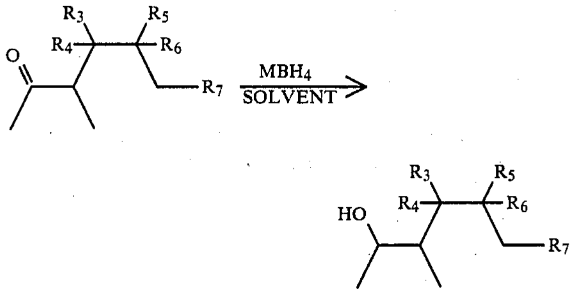

The alkali metal may be sodium, potassium or lithium and insofar as the most preferred and most expeditious reducing agent, sodium borohydride is the least expensive and most easily available. The reaction temperature is preferably between 20° C. and 50° C. The reaction preferably takes place in the presence of an inert solvent such as methanol, ethanol, isopropyl alcohol, or n-butanol. The concentration of ketone having the structure:

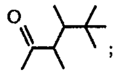; 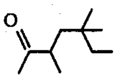 or 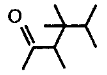

in the reaction mass may vary from about 100 grams per liter up to about 500 grams per liter. The mole ratio of alkali metal borohydride:ketone reactant may vary from about 0.2:1 up to about 1:1 with a preferred mole ratio of alkali metal borohydride:ketone being 1:2 or 0.5:1.

The resulting alcohol derivative defined according to one or more of the structures:

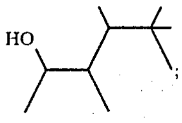; 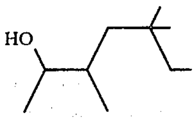 and/or

-continued

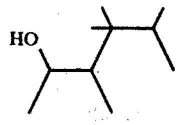

may be isolated from the reaction mass by first quenching unreacted alkali metal borohydride in a weak acid quench (e.g. 6 molar hydrochloric acid) and then washing the reaction mass with base, saturated sodium chloride and finally distilling the resulting reaction product in vacuuo.

In the alternative, the reaction product which is one or more of the compounds having the structures:

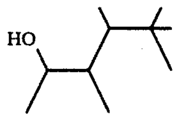
;
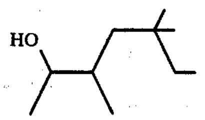
and

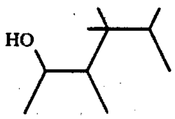

may be further reacted to form the acetic acid ester or acetates defined according to the structure:

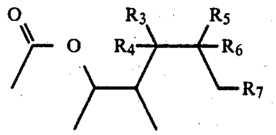

wherein $R_3$, $R_4$, $R_5$, $R_6$ and $R_7$ are defined supra. This reaction is carried out thusly:

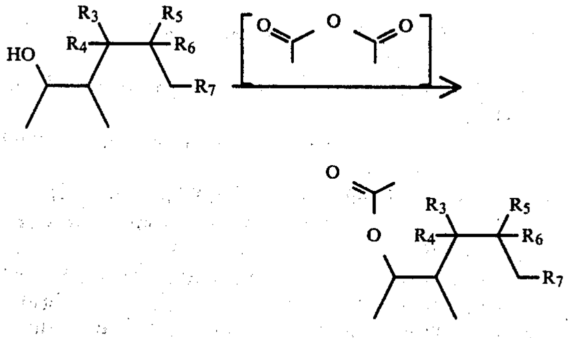

The reaction temperature is preferably in the range of from about 70° C. up to about 100° C. with a preferred reaction temperature of 80° C. at atmospheric pressure. The time of reaction may vary between 1.5 hours and 4 hours at about 80° C. The mole ratio of one or more of the alcohols having the structure:

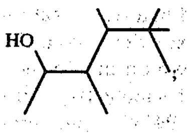
;
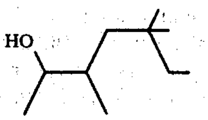
and/or

-continued

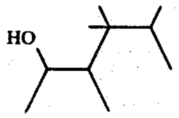

acetic anhydride may vary from about 1:1 down to 1:0.1.

At the end of the reaction, the reaction mass is cooled and the aqueous phase is separated from the organic phase. The organic phase is washed with one liter of concentrated sodium chloride solution followed by saturated sodium carbonate solution followed by saturated sodium chloride solution. The pH of the resulting solution should be in the range of from about 8 up to about 9.

The reaction mass is then dried using standard drying methods and distilled in a fractional distillation column preferably under vacuuo. The resultant product is dried and distilled on a fractional distillation column to yield perfume quality material. Such material has a fruity, woody and amber-like aroma. This differs from the alcohol prior to esterification which alcohol has a woody, camphoraceous, patchouli-like aroma.

As olfactory agents the methyl substituted oxohexane derivatives of our invention taken alone or in admixture can be formulated into or used as components of a "perfume composition" or can be used as components of a "perfumed article" or the perfume composition may be added to perfumed articles.

The term "perfume composition" is used herein to mean a mixture of organic compounds including, for example, alcohols (other than the alcohols of our invention), aldehydes, ketones, nitriles, ethers, esters (other than the esters of our invention), lactones, epoxides, natural essential oils, synthetic essential oils and hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation and (d) topnotes which are usually low-boiling, fresh-smelling materials.

In perfume compositions, the individual component will contribute its particular olfactory characteristics, but the overall effect of the perfume composition will be the sum of the effects of each of the ingredients and, in certain instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the methyl substituted oxohexane derivative(s) of this invention which will be effective in perfume compositions depends on many factors, including the other ingredients, their amounts and the effects which are desired. It has been found that perfume compositions containing as little as 0.05% of the methyl substituted oxohexane derivative(s) of this invention, or even less, can be used to impart interesting woody, camphoraceous, patchouli-like, fruity and amber-like aroma nuances to soaps, liquid or solid anionic, cationic, nonionic or zwitterionic detergents, cosmetics, cosmetic powders, liquid or solid fabric softeners, drier-added fabric softener articles, (e.g. BOUNCE®, a registered trademark of the Procter & Gamble Company of Cincinnati, Ohio), optical brightener compositions, hypochlorite bleach compositions, fragranced polymers, hair conditioners and other products. The amount employed can range up to 70% or even higher and will depend on considerations of cost, nature of the end product and the effect desired on the finished product and particular fragrance sought. Thus, for example, when fragrancing liquid bleach compositions containing alkali metal hypochlorite such as, for example, sodium hypochorite, for example CLOROX® (registered trademark of Clorox, Inc.), the amount employed can range as high as 100% of the fragrance involved in the liquid bleach. Indeed, a distinctive aspect of our invention is the use of one or more of the methyl substituted oxohexane derivative(s) in a stable liquid bleach composition.

The methyl substituted oxohexane derivative(s) of this invention taken alone or in admixture can be used alone or in a perfume composition as an olfactory component in detergents, soaps, space odorants and deodorants; perfumes; colognes, toilet waters; bath salts; hair preparations such as lacquers, brilliantines, pomades and shampoos; cosmetic preparations such as creams deodorants, hand lotions, sun screens; powders such as talcs, dusting powders, face powders and the like; liquid bleaches such as sodium hypochlorite-containing bleaches; floor waxes, automobile aromas and automobile polish compositions. When used as an olfactory component of a perfumed article as little as 0.01% of one or more of the methyl substituted oxohexane derivative(s) will suffice to impart an interesting a woody, camphoraceous, patchouli-like, fruity and amber-like odor. Generally no more than 1.5% is required to impart such aromas. However, in view of the rather low cost of the methyl substituted oxohexane derivative(s) of our invention, up to 100% of the perfume composition can be one or more of the methyl substituted oxohexane derivative(s).

In summary, the range of the methyl substituted oxohexane derivative(s) of our invention in the perfumed article can be from 0.01% up to 1.5% or even higher.

In addition, the perfume composition can contain a vehicle or carrier for the methyl substituted oxohexane derivative(s) alone or with other ingredients. The vehicle can be a liquid such as a non-toxic alcohol such as ethanol, a glycol such as propylene glycol or the like. The carrier can be an absorbent solid such as a gum or components for encapsulating the composition such as gelatin which can be used to form a capsule wall surrounding the perfume oil as by means of coacervation with gelation or as by means of formation of a polymer around the perfume oil as by polymerizing a urea formaldehyde polymer.

It will thus be apparent that the methyl substituted oxohexane derivatives of our invention can be used to alter, modify, augment or enhance sensory properties particularly organoleptic properties such as fragrances of a wide variety of consumable materials.

The following examples serve to illustrate our invention and this invention is to be considered restricted thereto only as indicated in the appended claims.

All parts and percentages given herein are by weight unless otherwise specified.

EXAMPLE A

Preparation of Diisoamylene Derivatives

Reaction:

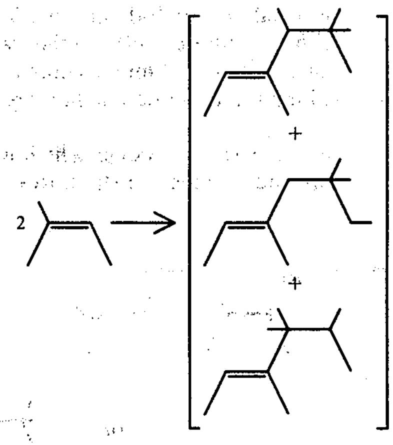

Diisoamylene is prepared according to one of the procedures set forth in the following references:

(i)—Murphy & Lane, Ind. Eng. Chem., Prod. Res. Dev., Vol. 14, No. 3, 1975, p. 167 (Title: Oligomerization of 2-Methyl-2-Butene in Sulfuric Acid and Sulfuric-Phosphoric Acid Mixtures).

(ii)—Whitmore & Mosher, Vol. 68, J. Am. Chem. Soc., February, 1946, p. 281 (Title: The Depolymerization of 3,4,5,5-Tetramethyl-2-Hexene and 3,5,5-Trimethyl-2-Heptene in Relation to the Dimerization of Isoamylenes).

(iii)—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv)—U.S. Pat. No. 3,627,700, issued on Dec. 14, 1971, (Zuech).

(v)—U.S. Pat. No. 3,538,181, issued on Nov. 3, 1970, (Banks).

(vi)—U.S. Pat. No. 3,461,184 issued on Aug. 12, 1969 (Hay, et al).

(vii)—Trusz, Chemische Zentralblatt, 1919, II 125 (Production of Di-isoamylene From Isoamylene Using Mercury Acetate Catalyst).

As an illustration and not by way of limitation, the following example sets forth the preparation of diisoamylenes useful in producing the methyl substituted oxohexane derivatives of our invention which are useful in producing the fragrances of our invention.

EXAMPLE A—I

OVer a period of 10 hours, 2-methyl-2-butene is pumped through a 5'×⅝" (0.625 inch) tube packed with 15.0 grams of polystyrene sulfonic acid catalyst at a temperature of 100° C. and a pressure of 400 psig.

The resulting material was distilled in a fractionation column in order to separate the diisoamylene from the higher molecular weight polymers which are formed during the reaction as by-products. This material distills at 36°-40° C. vapor temperature; 74°-94° C. liquid temperature and 4–5 mm/Hg pressure. This material will be used in the syntheses in the following Example II.

FIG. 1A represents the GLC profile for the reaction product of Example A using a 70% sulfuric acid catalyst at 35° C.

FIG. 1B represents the GLC profile for the reaction product of Example A using an Amberlyst® 15 acidic ion exchange catalyst at a temperature of 150° C.

FIG. 1C represents the GLC profile for the reaction product of Example A using an Amberlyst® 15 catalyst at 100° C.

FIG. 1D represents the GLC profile for the reaction product of Example A using a sulfuric acid catalyst and an alpha-methylstyrene diluent at 35° C. according to the conditions of United Kingdom Patent Specification No. 796,130 (crude reaction product).

FIG. 1E represents the GLC profile for the reaction product of Example A using a sulfuric acid catalyst at 35° C. and an alpha-methylstyrene diluent according to the conditions of United Kingdom Patent Specification No. 796,130 (distilled reaction product). Distillation range: 36°–40° C. vapor temperature for the diisoamylene; 74°–94° C. liquid temperature for the diisoamylene; and 4–5 mm/Hg pressure.

FIG. 2A represents the NMR spectrum for Peak 1 for the GLC profile of FIG. 1E.

FIG. 2B represents the infra-red spectrum for Peak 1 of the GLC profile of FIG. 1E.

FIG. 3A represents the NMR spectrum for Peak 2 of the GLC profile of FIG. 1E.

FIG. 3B represents the infra-red spectrum for Peak 2 of the GLC profile of FIG. 1E.

Figure 4:
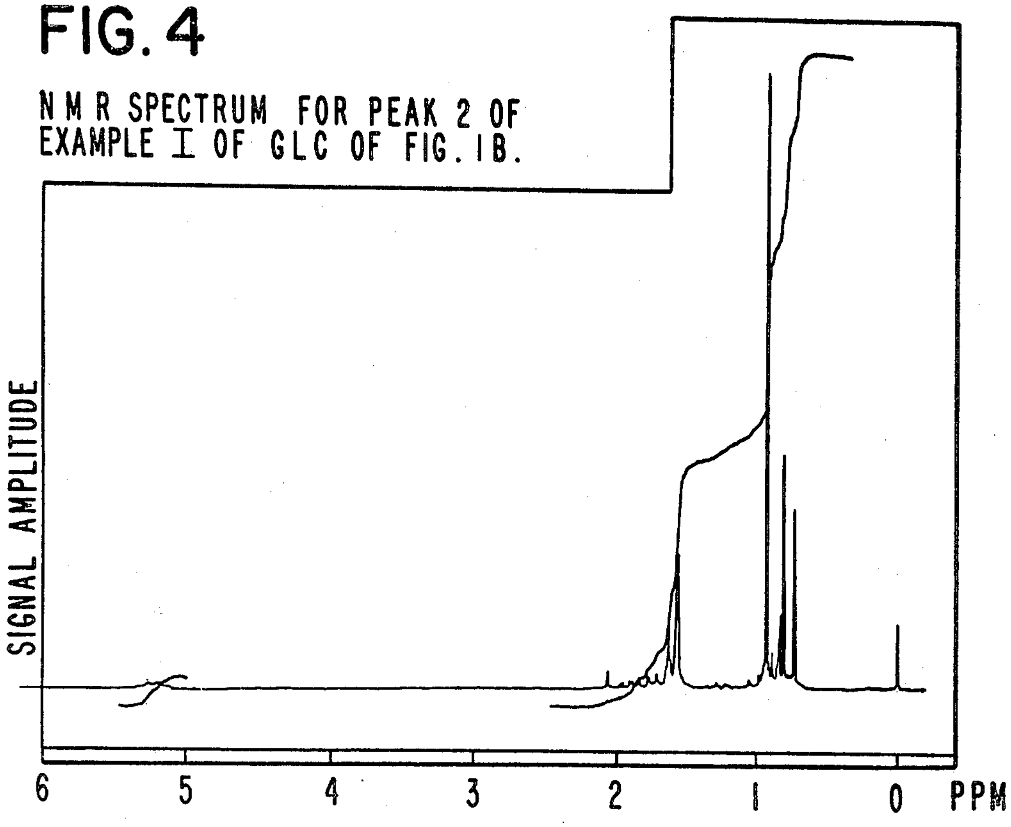
FIG. 4 represents the NMR spectrum for Peak 2 of the GLC profile of FIG. 1B.

FIG. 4 represents the NMR spectrum for Peak 2 of the GLC profile of FIG. 1B.

EXAMPLE I

Preparation of Methyl Substituted Oxohexane Derivatives

Reaction:

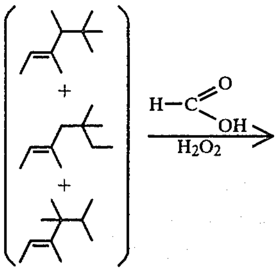

-continued

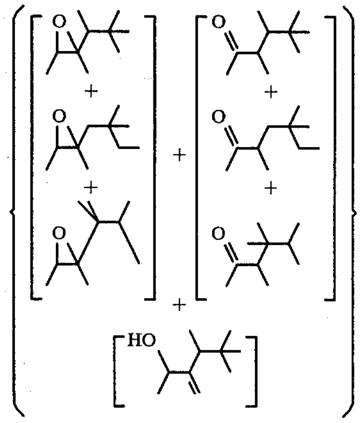

Into a 3 liter reaction flask equipped with stirrer, thermometer, reflux condenser, dropping funnel, heating mantle and cooling bath is placed 1,000 grams of diisoamylene prepared according to Example A-I (distillation temperature 36°–40° C. vapor temperature; 74°–94° C. liquid temperature at 4–5 mm/Hg pressure) and 375 grams of 90% formic acid. The resulting mixture is heated to 50° C. and then over a period of 1.25 hours 485 grams of 50% hydrogen peroxide is slowly added to the reaction mass while maintaining the reaction mass at a temperature in the range of 42°–69° C. After the addition of the hydrogen peroxide, the reaction mass is then heated at 50° C. for a period of 3.5 hours. At the end of the 3.5 hour period, the reaction mass is cooled to room temperature and 1 liter of a 25% aqueous sodium hydroxide solution is added to the reaction mass. The reaction mass is then again washed with 1 liter of 25% sodium hydroxide followed by 2 volumes of 500 ml saturated sodium chloride. The organic phase is then distilled on a 2′×1″ Goodloe column yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 54/60 | 93/105 | 25/35 | 9:1/9:1 | 25.8 |
| 2 | 64 | 105 | 35 | 9:1 | 30.9 |
| 3 | 68 | 105 | 45 | 9:1 | 36.4 |
| 4 | 80 | 107 | 50 | 9:1 | 32.2 |
| 5 | 88 | 107 | 50 | 9:1 | 36.2 |
| 6 | 93 | 109 | 50 | 9:1 | 36.3 |
| 7 | 95 | 109 | 50 | 9:1 | 39.0 |
| 8 | 96 | 110 | 50 | 9:1 | 34.9 |
| 9 | 96 | 111 | 50 | 9:1 | 36.8 |
| 10 | 96 | 112 | 50 | 9:1 | 38.8 |
| 11 | 97 | 113 | 50 | 9:1 | 44.3 |
| 12 | 97 | 114 | 50 | 9:1 | 45.8 |
| 13 | 99 | 116 | 50 | 9:1 | 45.6 |
| 14 | 99 | 119 | 50 | 9:1 | 45.9 |
| 15 | 100 | 120 | 50 | 9:1 | 40.3 |
| 16 | 103 | 125 | 50 | 9:1 | 45.6 |
| 17 | 104 | 134 | 50 | 9:1 | 50.5 |
| 18 | 107 | 140 | 50 | 9:1 | 39.6 |
| 19 | 86 | 141 | 10 | 9:1 | 38.3 |
| 20 | 150 | 152 | 10 | 9:1 | 19.2 |

Fractions 6–15 (boiling range 93°–100° C. vapor temperature; 109°–120° C. liquid temperature and 50 mm/Hg pressure) is bulked and evaluated from an organoleptic standpoint. Fractions 6–15 has a fruity, eucalyptus and hay-like aroma.

FIG. 5 is the GLC profile of the reaction product prior to distillation. FIG. 5 is described in detail in the section entitled "Detailed Description of the Drawings", supra.

FIG. 6 is the NMR spectrum for Peaks 31, 32 and 33 of FIG. 5 containing the compounds having the structures:

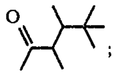 ; 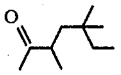 and 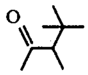

FIG. 7 is the IR spectrum for Peaks 31, 32 and 33 of FIG. 5 containing the compounds having the structures:

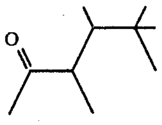 ; 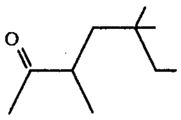 and 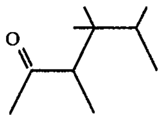

FIG. 8 is the NMR spectrum for Peaks 21, 22 and 23 of FIG. 5 containing epoxy diisoamylenes.

FIG. 9 is the infra-red spectrum for Peaks 21, 22 and 23 of FIG. 5 containing epoxy diisoamylenes.

EXAMPLE II

Preparation of Methyl Substituted Oxohexane Derivatives Which Are Alcohols

Reaction:

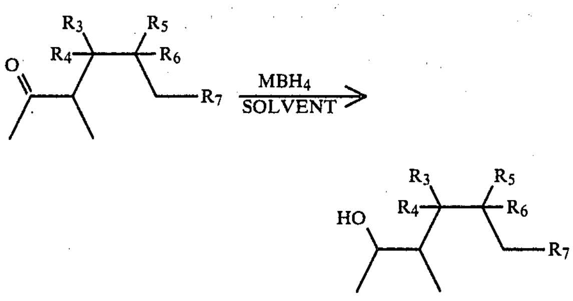

wherein M is sodium and $R_3$, $R_4$, $R_5$, $R_6$ and $R_7$ are defined supra.

Into a three-liter reaction flask is charged 1,000 ml isopropyl alcohol and 54 grams of sodium borohydride. 428 grams of the methyl substituted oxohexane derivative mixture (ketones) prepared according to Example I, bulked fractions 6–15, consisting of the compounds having the structure:

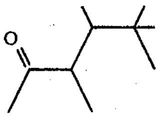 ; 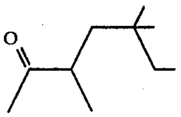 and 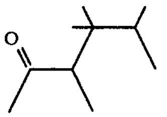

are then added over a period of one hour to the reaction mass while maintaining the reaction mass at a temperature of 20°–40° C. At the end of the addition of the ketone mixture, the reaction mass is quenched with six molar hydrochloric acid. The reaction mass is then heated to 40° C. and maintained at 40° C. for a period of 25 hours. The reaction mass is then poured into 1,000 ml of six molar hydrochloric acid over a period of two hours during which time hydrogen gas is released. Ice water cooling is applied. The reaction mass is then added to one kilogram of 25% aqueous sodium hydroxide. The aqueous phase is separated from the organic phase and the organic phase is washed with two one-liter portions of saturated sodium chloride. The crude material is then washed with water yielding 854 grams of product.

The product is distilled on a 1"×12" Goodloe column yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 87 | 95 | 13 | 1:1 | 27 |
| 2 | 88 | 96 | 13 | 1:1 | 24 |
| 3 | 89 | 96 | 14 | 1:1 | 18 |
| 4 | 90 | 97 | 14 | 1:1 | 23 |
| 5 | 90 | 97 | 14 | 1:1 | 20 |
| 6 | 91 | 98 | 14 | 1:1 | 22 |
| 7 | 91 | 99 | 14 | 1:1 | 22 |
| 8 | 92 | 99 | 14 | 1:1 | 25 |
| 9 | 97 | 99 | 14 | 1:1 | 28 |
| 10 | 93 | 99 | 14 | 1:1 | 22 |
| 11 | 93 | 108 | 14 | 1:1 | 21 |
| 12 | 95 | 117 | 14 | 1:1 | 21 |
| 13 | 78 | 158 | 3 | 1:1 | 17 |
| 14 | 75 | 170 | 4 | 1:1 | 2 |

Fractions 5–11 are bulked for evaluation and for further reaction with acetic acid in Example III. Fractions 5–11 have a woody, camphoraceous, patchouli-like aroma.

FIG. 10 is the GLC profile of the crude prior to distillation (conditions: 10'×¼" Carbowax 68 column programmed at 100°–220° C. at 8° C. per minute).

FIG. 11 is the GLC profile for fraction 1 of the foregoing distillation (conditions: 10'×¼" Carbowax 68 column programmed at 100°–220° C. at 8° C. per minute).

FIG. 12 is the GLC profile for fraction 3 of the foregoing distillation (conditions: 10'×¼" Carbowax 68 column programmed at 100°–220° C. at 8° C. per minute).

FIG. 13 is the GLC profile for fraction 5 of the foregoing distillation (conditions: 10'×¼" Carbowax 68 column programmed at 100°–220° C. at 8° C. per minute).

FIG. 14 is the infra-red spectrum for bulked fractions 5–11 of the foregoing distillation.

FIG. 15 is the NMR spectrum for bulked fractions 5–11 of the foregoing distillation.

EXAMPLE III

Preparation of Diisoamylol Acetate

Reaction:

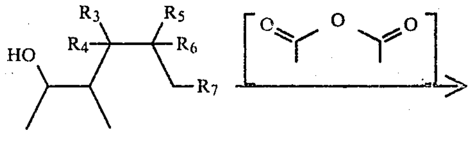

-continued

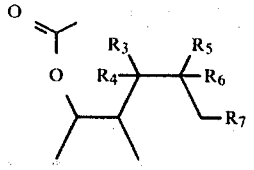

wherein $R_3$, $R_4$, $R_5$, $R_6$ and $R_7$ are defined supra.

Into a one liter reaction flask is charged 250 grams of acetic anhydride. The acetic anhydride is heated to 80° C. and at that point in time and over a period of two hours while maintaining the reaction mass at 80° C., 200 grams of bulked fractions 5-11 of the distillation product of the reaction product of Example II supra is added to the reaction mass. This reactant contains the compounds having the structures:

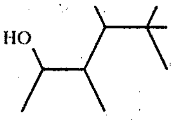
;
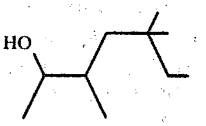
and

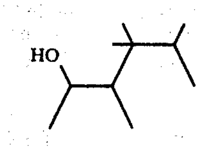

At the end of the reaction, 100 ml water is added to the reaction product and the reaction mass is stirred at 80° C. for a period of one hour. The organic phase is then separated from the aqueous phase and the organic phase is added to one liter of 10% sodium chloride solution. The organic phase is then washed as follows:

(i) one 500 ml portion 10% Hcl;

(ii) one 500 ml portion of saturated sodium carbonate;

(iii) one 500 ml portion of saturated sodium chloride.

The crude weighs 226 grams.

The resulting crude is distilled on a Vigreus column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 81/86 | 92/92 | 8.5 | 21 |
| 2 | 86 | 94 | 8.5 | 26 |
| 3 | 87 | 99 | 8.3 | 24 |
| 4 | 87 | 99 | 8.5 | 19 |
| 5 | 88 | 97 | 8.5 | 21 |
| 6 | 88 | 97 | 8.5 | 24 |
| 7 | 89 | 97 | 8.5 | 24 |
| 8 | 90 | 100 | 8.5 | 25 |
| 9 | 90 | 104 | 8.5 | 19 |
| 10 | 92 | 165 | 8.0 | 15 |

Fractions 5-9 are bulked and utilized in the following perfume utility examples, infra. Fractions 5-9 have a fruity, woody, dry, ambery aroma.

FIG. 16 is the GLC profile for the crude reaction product prior to distillation (conditions: 10'×¼" Carbowax 68 column programmed at 100°-220° C. at 8° C. per minute).

FIG. 17 is the NMR spectrum for bulked fractions 5-9 of the foregoing distillation.

FIG. 18 is the infra-red spectrum for bulked fractions of the foregoing distillation.

EXAMPLE IV

The methyl substituted oxohexane derivatives produced according to Examples II and III have aromas which may be utilized to a great extent in inexpensive functional products. The following pine fragrance demonstrates the use of the materials produced according to Examples II and III in perfume compositions. In these cases they are used in concentrations of 47.9%:

| Ingredient | Example IV(A) | Example IV(B) |
|---|---|---|
| Mixture of alcohols produced according to Example II, bulked fractions 5-11 | 479 | 0 |
| Acetates produced according to Example III, bulked fractions 5-9 | 0 | 479 |
| Isobornyl acetate | 100 | 100 |
| Camphor | 10 | 10 |
| Terpineol | 25 | 25 |
| Fir balsam absolute (50% in diethyl phthalate) | 20 | 20 |
| Coumarin | 4 | 4 |
| Linalool | 30 | 30 |
| Anethol | 2 | 2 |
| Fenchyl alcohol | 10 | 10 |
| Lemon terpenes | 50 | 50 |
| Borneol | 5 | 5 |
| Turpentine Russian | 150 | 150 |
| Pinus pumilionus | 50 | 50 |
| Eucalyptol | 50 | 50 |
| 2,2,6-trimethyl-1-cyclohexene-1-carboxaldehyde | 5 | 5 |
| Maltol (1% in diethyl phthalate) | 5 | 5 |

The presence of the mixture of alcohols produced according to Example II having the structures:

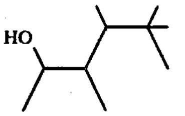
;
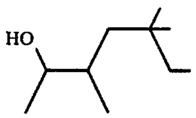
and

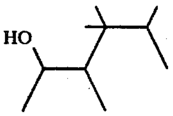

(bulked fractions 5-11) imparts to the composition of Example IV(A) woody, camphoraceous and patchouli-like nuances. The mixture of acetates produced according to Example III (bulked fractions 5-9) having the structures:

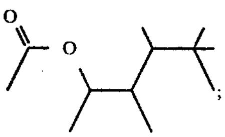
;

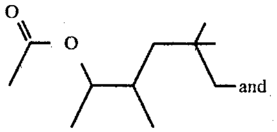
and

-continued

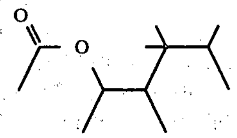

imparts to the composition of Example IV(B) fruity, woody, dry, and ambery nuances. Thus, the fragrances of Example IV(A) and IV(B) can be described as follows:

Example IV(A)—a pine aroma with woody, camphoraceous and patchouli-like undertones.

Example IV(B)—a pine aroma with fruity, woody and ambery undertones.

EXAMPLE V

Preparation of a Cosmetic Powder Composition

A cosmetic powder is prepared by mixing in a ball mill 100 grams of talcum powder with 0.25 grams of a perfume substance as set forth in Table I below. The resulting powder has an excellent aroma as set forth in Table I below:

TABLE I

| Perfume Substance | Aroma Description |
|---|---|
| Mixture of alcohols having the structures: 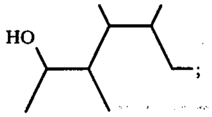 ; 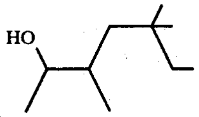 and 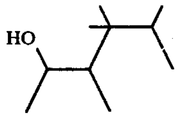 produced according to Example II, bulked fractions 5-11. | A woody, camphoraceous and patchouli-like aroma. |
| Mixture of acetates having the structures: 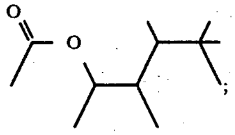 ; 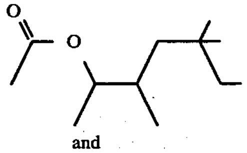 and 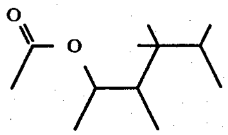 produced according to Example III, bulked fractions 5-9. | A fruity, woody and ambery aroma. |
| Perfume composition of Example IV(A) | A pine aroma with woody, camphoraceous and patchouli-like undertones. |
| Perfume composition of Example IV(B) | A pine aroma with fruity, woody and ambery undertones. |

EXAMPLE VI

Perfume Liquid Detergent

Concentrated liquid detergent (lysine salt of n-dodecylbenzene sulfonic acid as more specifically described in U.S. Pat. No. 3,948,818, issued on Apr. 6, 1976, the specification for which is incorporated herein by reference) with aroma nuances as set forth in Table I of Example V supra are prepared containing 0.10%, 0.15%, 0.20%, 0.25%, 0.30% and 0.35% of the substances as set forth in Table I of Example V supra. They are prepared by adding and homogeneously mixing the appropriate quantity of fragrance formulation of Table I of Example V supra in the liquid detergents. The detergents all possess excellent aromas, the intensity increasing with greater concentration of perfume substance of Table I of Example V.

EXAMPLE VII

Preparation of a Cologne and Handkerchief Perfume

The perfume substances as set forth in Table I of Example V supra are incorporated into colognes at concentrations of 2.0%, 2.5%, 3.0%, 3.5%, 4.0%, 4.5% and 5.0% in 75%, 80%, 85% and 90% aqueous food grade ethanol; and into handkerchief perfumes at concentrations of 15%, 20%, 25% and 30% (in 80%, 85%, 90% and 95% aqueous food grade ethanol solutions). Distinctive and definitive aroma nuances as set forth in Table I of Example V are imparted to the colognes and to the handkerchief perfumes at all levels indicated above.

EXAMPLE VIII

Preparation of Soap Compositions

One hundred grams of soap chips (IVORY®, produced by the Procter & Gamble Company of Cincinnati, Ohio) are mixed with 1 gram of each of the perfumery substances of Table I of Example V, supra until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table I of Example V supra.

EXAMPLE IX

Preparation of Solid Detergent Compositions

A detergent is prepared from the following ingredients according to Example I of Canadian Pat. No. 1,007,948, (the specification for which is incorporated herein by reference):

| Ingredient | Percent by Weight |
|---|---|
| Neodol® 45-11 (a $C_{14}$-$C_{15}$ | 12 |

-continued

| Ingredient | Percent by Weight |
|---|---|
| alcohol ethoxylated with 11 moles of ethylene oxide) | |
| Sodium carbonate | 55 |
| Sodium citrate | 20 |
| Sodium sulfate, water brighteners | q.s. |

This detergent is phosphate-free detergent. A total of 100 grams of said detergent is admixed with 0.10, 0.15, 0.20 and 0.25 grams of the substances of Table I of Example V supra. The detergent samples in each case have excellent aromas as set forth in Table I of Example V supra.

EXAMPLE X

Utilizing the procedure of Example I at column 15 of U.S. Pat. No. 3,632,396, (the disclosure of which is incorporated by reference herein) a nonwoven cloth substrate useful as a drier-added fabric softening article of manufacture is prepared wherein the substrate, the substrate coating and the outer coating and the perfuming material are as follows:

1. A water dissolvable paper ("Dissolvo Paper");
2. Adogen 448 (melting point about 140° F.) as the substrate coating; and
3. An outer coating having the following formulation (melting point about 150° F.):
   - 57% $C_{20-22}$ HAPS
   - 22% isopropyl alcohol
   - 20% antistatic agent
   - 1% of one of the perfume substances of Table I of Example V, supra.

Fabric softening compositions having aromas as set forth in Table I of Example V are prepared which essentially consist of a substrate having a weight of about 3 grams per 100 square inches; a substrate coating having a weight of about 1.85 grams per 100 grams of substrate; and an outer coating having a weight of about 1.4 grams per 100 square inches of substrate, thereby providing a total aromatized substrate and outer coating weight ratio of about 1:1 by weight of the substrate. The aromas as set forth in Table I of Example V are imparted in a pleasant manner to the head space in the drier on operation thereof using each of the drier-added fabric softening nonwoven fabric samples.

In the following examples, Aromox® DMC-W and Aromox® DMMC-W are 30% aqueous solutions of dimethyl cocoamine oxide; and Aromox® NCMDW is a 40% aqueous solution of N-cocomorpholine oxide produced by Armac Division of ADZO of Chicago, Ill.

EXAMPLE XI

Four drops of one or more of the perfume substances as set forth in Table I of Example V supra is added to 2 grams of Aromox® DMC-W to produce a clear premix. The clear premix is added to 200 grams of CLOROX® with stirring resulting in a clear, stable, single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint, pleasant aroma as set forth in Table I of Example V supra. Furthermore, no such characteristic "hypochlorite" aroma is retained on the hands of the individual handling such laundry in both the wet and the dry states.

EXAMPLE XII

Aromox® DMMC-W in various quantities is mixed with 0.1 grams of each of the substances of Table I of Example V supra. The resulting premixes are then added to 200 grams of an aqueous 5% sodium hypochlorite solution. Sufficient 12.5 M aqueous NaOH is added to bring the pH of each of the mixtures up to 13. The following results are obtained:

| Percentage Aromox® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days |

When the 5% aqueous sodium hypochlorite solutions are used as laundry bleaches, the resulting laundry batches on dry-out in an atmosphere of 65% relative humidity yields substantially no characteristic "hypochlorite" odor but do have faint, pleasant aromas as set forth in Table I of Example V supra. Furthermore, no such characteristic "hypochlorite" aroma is retained on the hands of the individual handling such laundry batches in both the wet and the dry states.

EXAMPLE XIII

Two grams of Aromox® DMMC-W are admixed with eight drops of each of the perfume substances of Table I of Example V supra. Each of the premixes is then added with stirring to 200 grams of a 7% aqueous solution of lithium hypochlorite. Sufficient 3 M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain an aroma as described in Table I of Example V whereas without the use of the substances of Table I of Example V, the bleached laundry batches have faint characteristic disagreeable "hypochlorite" aromas.

EXAMPLE XIV

Two grams of Aromox® DMMC-W are admixed with eight drops of each of the substances of Table I of Example V supra. The premixes are then added with stirring to 200 grams of a mixture containing 4.5% aqueous sodium hypochlorite and 4.5% aqueous lithium hypochlorite. Sufficient 4 M aqueous LiOH is added to bring the pH of the solutions to 13.4. The mixtures are then heated to 120° F. and maintained at that temperature for a period of one week. The resulting solutions remain clear in a single phase. When used as laundry bleach, the resulting bleached laundry batches on dry-out in an atmosphere of 50% relative humidity retain an aroma as set forth in Table I of Example V supra whereas without the use of the perfume substances as set forth in Table I of Example V supra, the bleached laundry batches have faint characteristic and disagreeable "hypochlorite" aromas.

EXAMPLE XV

Two grams of Aromox® DMMC-W are admixed with eight drops of one of the perfume substances of Table I of Example V supra. These premixes are then added with stirring to 200 grams of mixture containing 4% aqueous sodium hypochlorite and 4% aqueous lithium hypochlorite. Sufficient 2 M aqueous NaOH is added to bring the pH of the solutions to 13.4. The mixtures are then heated to 110° F. and maintained at that temperature with stirring for a period of two weeks. The resulting solutions remain clear as a single phase when used as laundry bleaches. The resulting bleached laundry batches on dry-out in an atmosphere of 50% relative humidity retain aromas as set forth in Table I of Example V supra whereas without the use of the perfurme substances of Table I of Example V supra, the bleached laundry batches have faint, characteristic disagreeable "hypochlorite" aromas.

EXAMPLE XVI

Four drops of each of the substances of Table I of Example V supra are added to 1.5 grams of Aromox® NCMDW to produce a clear premix. The clear premixes are added to 200 grams in each case of CLOROX® with stirring resulting in a clear single phase solution. Sufficient 1 M aqueous NaOH is added to bring the pH of the mixture up to 12.8. The solution remains substantially stable at 120° F. for a period of 7 days. When the 5% aqueous sodium hypochlorite solutionn is used as a laundry bleach, the resulting laundry on dry-out in an atmosphere of 65% relative humidity yields substantially no characteristic hypochlorite aroma but does have a faint pleasant aroma as set forth in Table I of Example V supra. Furthermore, no such characteristic "hypochlorite" aroma is retained on the hands of the individual handling such laundry in both the wet and the dry states.

EXAMPLE XVII

Four drops of each of the substances of Table I of Example V supra are added to 1 gram of n-undecyl dimethyl amine oxide to produce a clear premix in each case. The clear premix is added to 200 grams of CLOROX® with stirring resulting in a clear, single phase solution. Sufficient 1 M aqueous NaOH is added to bring the pH of the mixture to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic hypochlorite odor but does have a faint pleasant odor as set forth in Table I of Example V supra. Furthermore, no such characteristic "hypochlorite" odor is retained on the hands of the individual handling such laundry in both the wet and the dry states.

EXAMPLE XVIII

Four drops of each of the substances of Table I of Example V supra is added to 1 gram of n-dodecyl dimethyl amine oxide to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant aroma as set forth in Table I of Example V supra. Furthermore, no such characteristic "hypochlorite" aroma is retained on the hands of the individual handling such laundry in both the wet and the dry states.

EXAMPLE XIX

One gram of n-tridecyl dimethyl amine oxide is admixed with eight drops of each of the substances of Table I of Example V supra. Each of the premixes is then, with stirring, added to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains an aroma as set forth in Table I of Example V supra; whereas without the use of any of the substances of Table I of Example V supra, the bleached laundry has a faint, characteristic, disagreeable "hypochlorite" aroma.

What is claimed is:

1. A process for augmenting or enhancing the aroma of a perfume composition, cologne or perfumed article comprising the step of intimately admixing with the perfume composition or cologne or perfumed article, an aroma augmenting or enhancing quantity of a product produced according to the process consisting of the steps of:

(i) dimerizing two moles of isoamylene in the presence of an acidic atalyst to form diisoamylene which is a mixture of molecules having the structures:

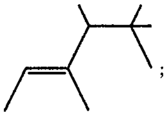
;
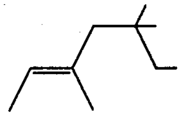
and
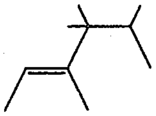

having a distillation range of 36°–40° C., vapor temperature; 74°–94° C. liquid temperature and 4–5 mm/Hg pressure;

(ii) intimately admixing the resulting diisoamylene mixture with concentrated hydrogen peroxide and formic acid whereby a mixture of alcohols, epoxides and ketones is formed according to the reaction:

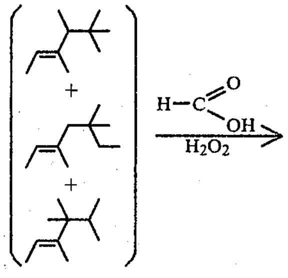

-continued

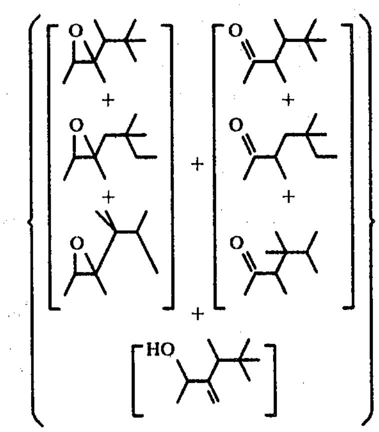

(iii) distilling the resulting reaction product at a temperature in the range of 93°-100° C. vapor temperature; 109°-120° C. liquid temperature at 50 mm/Hg pressure in order to isolate a mixture of compounds having the structure:

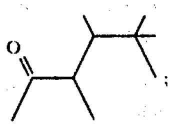 ; 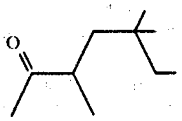 and 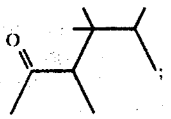 ;

and (iv) intimately admixing the resulting mixture with an alkali metal borohydride whereby a mixture of compounds is formed having the structures:

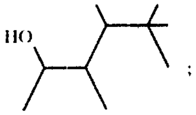 ; 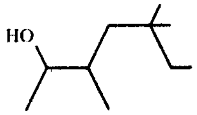 and

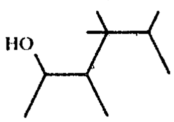

distilling at a vapor temperature in the range of 90°-93° C.; a liquid temperature in the range of 97°-108° C. and a pressure of 14 mm/Hg.

2. A process for augmenting or enhancing the aroma of a perfume composition, cologne or perfumed article comprising the step of intimately admixing with the perfume composition or cologne or perfumed article an aroma augmenting or enhancing quantity of a product produced according to the process consisting essentially of the steps of:

(i) dimerizing two moles of isoamylene in the presence of an acidic atalyst to form diisoamylene which is a mixture of molecules having the structures:

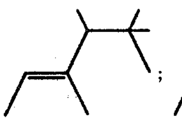 ; 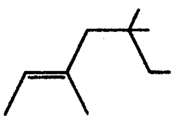 and 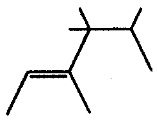

having a distillation range of 36°-40° C., vapor temperature; 74°-94° C. liquid temperature and 4-5 mm/Hg pressure;

(ii) intimately admixing the resulting diisoamylene mixture with concentrated hydrogen peroxide and formic acid whereby a mixture of alcohols, epoxides and ketones is formed according to the reaction:

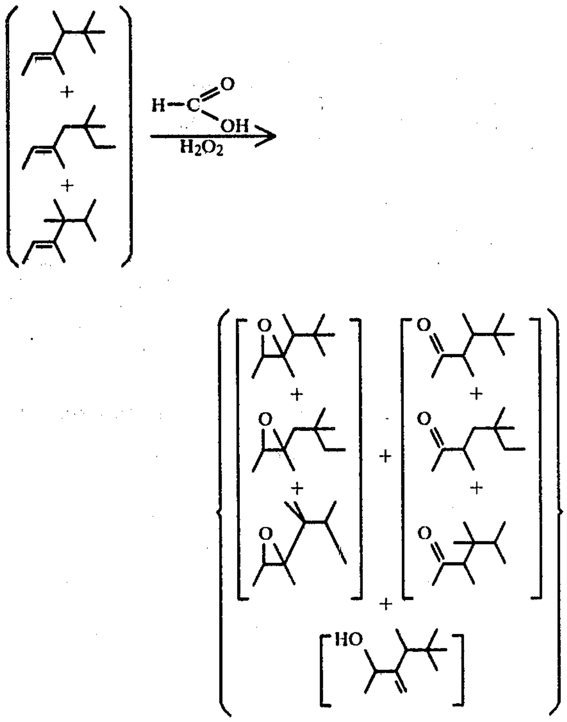

(iii) distilling the resulting reaction product at a temperature in the range of 93°-100° C. vapor temperature; 109°-120° C. liquid temperature at 50 mm/Hg pressure in order to isolate a mixture of compounds having the structure:

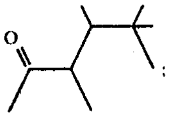 ; 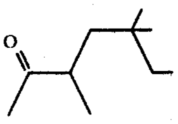 and 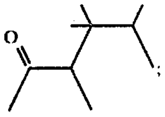 ;

(iv) intimately admixing the resulting mixture with an alkali metal borohydride whereby a mixture of compounds is formed having the structures:

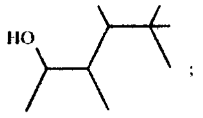 ; 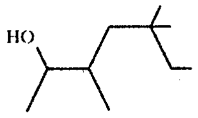 and

-continued

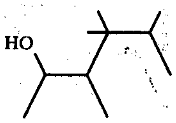

distilling at a vapor temperature in the range of 90°-93° C.; a liquid temperature in the range of 97°-108° C. and a pressure of 14 mm/Hg; and (v) intimately admixing the mixture of compounds having the strutures:

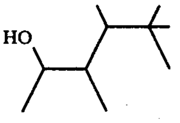
;
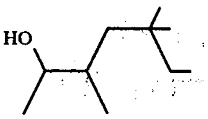
and
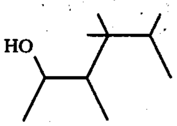

with acetic anhydride whereby a mixture of compounds is formed having the structures:

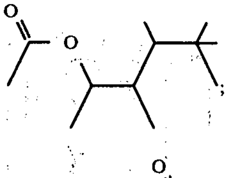
;
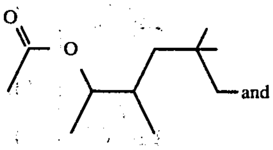
and
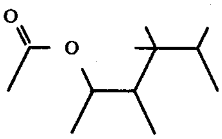

distilling at a vapor temperature in the range of 88°-90° C.; a liquid temperature in the range of 97°-109° C. and a pressure of 8.5 mm/Hg.

3. The process of claim 1 wherein the consumable material is a perfume composition or cologne.

4. The process of claim 2 wherein the consumable material is a perfume composition or cologne.

5. The process of claim 1 wherein the consumable material is a perfumed article and the perfumed article is a solid or liquid anionic, cationic, nonionic or zwitterionic detergent.

6. The process of claim 2 wherein the consumable material is a perfumed article and the perfumed article is a solid or liquid anionic, cationic, nonionic or zwitterionic detergent.

* * * * *